(12) United States Patent  
Standley

(10) Patent No.: US 12,227,349 B2
(45) Date of Patent: Feb. 18, 2025

(54) SYSTEM AND METHOD FOR PROVIDING AND ASSEMBLING AN AUTO-INJECTOR

(71) Applicant: Windgap Medical, Inc., Watertown, MA (US)

(72) Inventor: Adam Standley, Boston, MA (US)

(73) Assignee: Windgap Medical, Inc., Watertown, MA (US)

( * ) Notice: Subject to any disclaimer, the term of this patent is extended or adjusted under 35 U.S.C. 154(b) by 996 days.

(21) Appl. No.: 16/762,034

(22) PCT Filed: Nov. 8, 2018

(86) PCT No.: PCT/US2018/059755
§ 371 (c)(1),
(2) Date: May 6, 2020

(87) PCT Pub. No.: WO2019/094547
PCT Pub. Date: May 16, 2019

(65) Prior Publication Data
US 2020/0338258 A1    Oct. 29, 2020

Related U.S. Application Data

(60) Provisional application No. 62/582,969, filed on Nov. 8, 2017.

(51) Int. Cl.
*A61M 5/00* (2006.01)
*B65D 25/10* (2006.01)
(Continued)

(52) U.S. Cl.
CPC ......... *B65D 77/2024* (2013.01); *A61M 5/002* (2013.01); *B65D 25/108* (2013.01);
(Continued)

(58) Field of Classification Search
CPC ...... B65D 25/108; B65D 77/2024; A61J 1/16; A61M 5/002; A61M 5/001; A61M 5/008
(Continued)

(56) References Cited

U.S. PATENT DOCUMENTS 6,722,054 B2    4/2004  Yarborough et al.
6,907,679 B2 *  6/2005  Yarborough ............ A61P 35/00
                                                  34/287
(Continued)

FOREIGN PATENT DOCUMENTS

WO    WO2016/166765     * 10/2016 ............. A61M 5/00
WO    WO-2016/166769 A1   10/2016
WO    WO-2017/132554 A1    8/2017

OTHER PUBLICATIONS

International Search Report and Written Opinion for International Application No. PCT/US18/59755 dated Feb. 28, 2019.
(Continued)

*Primary Examiner* — Steven A. Reynolds
(74) *Attorney, Agent, or Firm* — Stephen J. Kenny; Foley Hoag LLP

(57) ABSTRACT

A component storage and nest system, the system including a tub having a lip portion provided on an interior surface of the tub; a primary nest having a plurality of receptacles in an upper surface, the upper surface having a flange portion about a perimeter being configured to engage the tub about the lip portion; and a plurality of medical components, a medical component being provided in each of the plurality of receptacles.

12 Claims, 24 Drawing Sheets

(51) Int. Cl.
*B65D 77/20* (2006.01)
*A61M 5/20* (2006.01)

(52) U.S. Cl.
CPC ........... *A61M 5/20* (2013.01); *A61M 2207/00* (2013.01); *A61M 2207/10* (2013.01); *Y10T 29/49826* (2015.01)

(58) Field of Classification Search
USPC ........................................ 206/571, 364, 438
See application file for complete search history.

(56) References Cited

U.S. PATENT DOCUMENTS

| | | | |
|---|---|---|---|
| 8,460,622 B2* | 6/2013 | Motadel | B01L 3/0275 422/526 |
| 9,630,745 B2 | 4/2017 | Lepot | |
| 9,718,583 B2* | 8/2017 | Nicoletti | B65D 65/02 |
| 2001/0042317 A1 | 11/2001 | Yarborough et al. | |
| 2005/0236346 A1* | 10/2005 | Whitney | B01L 9/06 211/74 |
| 2006/0016156 A1 | 1/2006 | Bush et al. | |
| 2010/0307956 A1 | 12/2010 | Lepot | |
| 2013/0015108 A1 | 1/2013 | Krauss et al. | |
| 2013/0048531 A1 | 2/2013 | Nicoletti | |
| 2013/0161225 A1* | 6/2013 | Lepot | B65D 25/00 206/557 |
| 2013/0186793 A1* | 7/2013 | Gagnieux | A61M 5/002 206/364 |
| 2014/0331618 A1 | 11/2014 | Guggisberg et al. | |
| 2015/0108020 A1* | 4/2015 | Iwase | A61M 5/008 206/365 |
| 2015/0190566 A1* | 7/2015 | Okihara | A61M 5/3134 206/365 |
| 2017/0183113 A1 | 6/2017 | Deutschle et al. | |

OTHER PUBLICATIONS

Supplementary European Search Report for EP Application No. 18876983.0 dated Jul. 23, 2021.

* cited by examiner

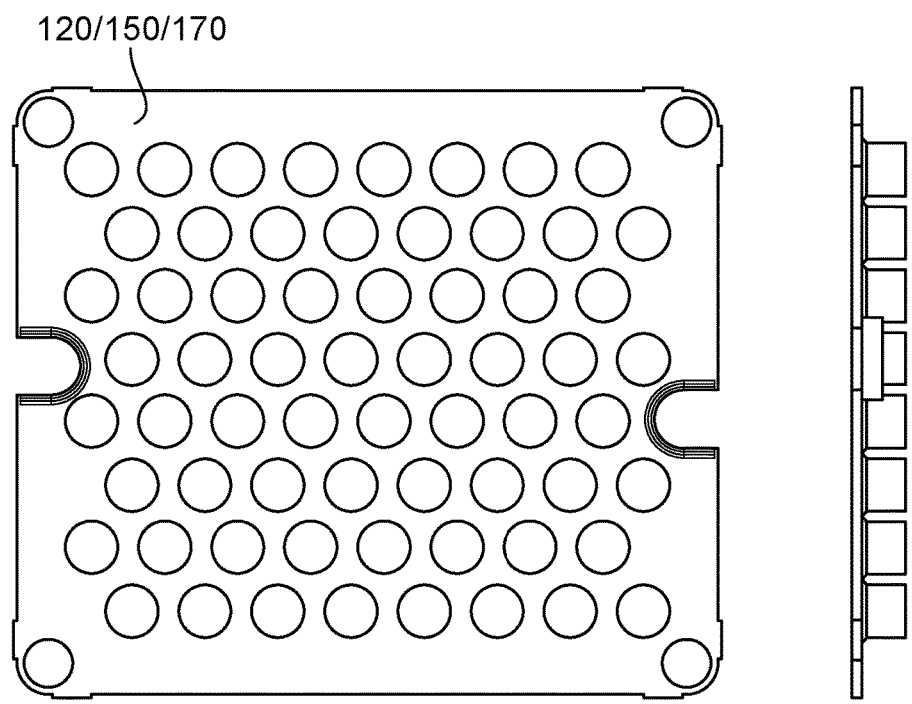
FIG. 10A
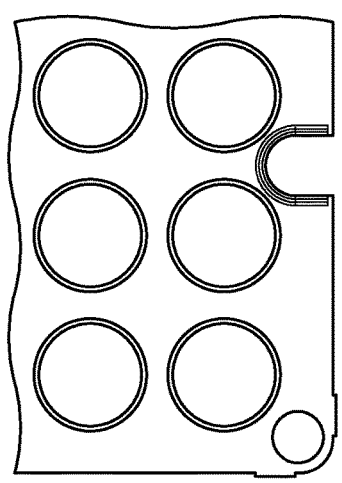
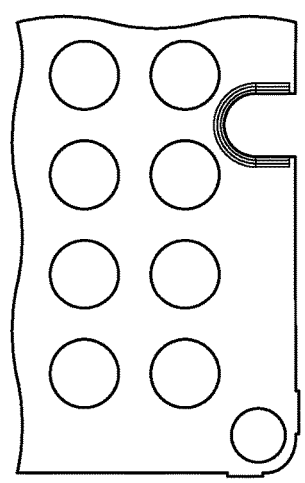
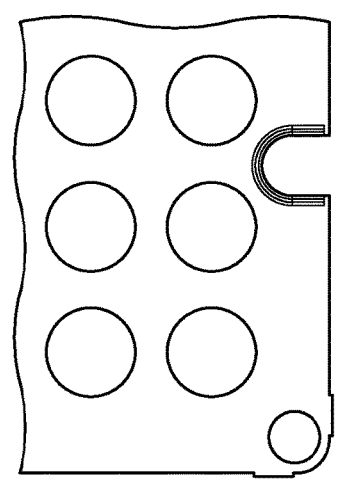
FIG. 10B        FIG. 10C        FIG. 10D

SYSTEM AND METHOD FOR PROVIDING AND ASSEMBLING AN AUTO-INJECTOR

CROSS-REFERENCE TO RELATED APPLICATIONS

This application claims the benefit of U.S. Provisional. Patent Application No. 62/582,969 filed on Nov. 8, 2017, which is all herein incorporated by reference in its entirety.

FIELD OF THE INVENTION

The present invention relates generally to the assembling and handling of auto-injectors and prefilled syringes and more particularly to transporting components thereof in a clean and controlled manner.

BACKGROUND OF THE INVENTION

In the field of medical device assembly, it is of particular importance to preserve the sterility of various components as they are assembled. In the particular field of auto-injectors the various parts are extremely small and are often assembled in sterile environments through the use of robotic means. It is then of particular importance to provide the various components using methods that can provide precise placement in sterile environments such that the robotic components can easily grasp and manipulate the components as necessary.

SUMMARY OF THE INVENTION

In one aspect of the present invention an ISO-tray, for example, an ISO standard 11040 11040-7, or tub is provided which has predetermined dimensions and fits into a receiving bay for later access by a robotic arm or other assembly steps. In some embodiments, the robot can then remove individual components being precisely located within a nest inside the tub for combination with other components being located in other receiving bays or perform necessary functions to or with each particular part.

In some embodiments, one or more nests can be provided at a first assembly station wherein the nests are filled with a plurality of components, which may require previously performed assembly steps. The ISO-tray or tub can be sealed and transported to a different location or station for additional steps, such as filling, lyophilization of liquids, etc. In one embodiment, and as discussed in more detail below, an ISO-tub can be provided with an interior lip designed to receive a nest. The nest can include a plurality of apertures or receptacles configured to receive a particular component. Each receptacle can include one or more retention clips or other retention features so as to ensure proper placement and orientation of the particular component of an assembly, i.e. the auto-injector, cartridge and/or syringe components. The robot or manually operated equipment can then be provided with a lifting tool configured to both grasp a component in each receptacle and simultaneously disengage the retention clips in a suitable manner.

In yet additional embodiments, a secondary nest can be configured to be placed into the first nest such that instead of inserting the ISO tub into the receiving bay of the robotic component, the nest can be inverted or removed and only the nest provided into the receiving bay of the robotic component. It will be appreciated that in some instances that an optimal storing orientation may differ from an optimal robotic grasping orientation, as such the one or more nests can be manipulated in various configurations so as to allow for proper placement.

Some of the nest embodiments can be configured to be flush with a top portion of the ISO-tub, be provided with stands on a top surface to aid in supporting the nest when inverted, or a de-nesting tray can be provided in conjunction with the nest so as to partially eject each of the components and thus provide a proper grasping surface for the robotic assembly means.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention, wherein:

FIG. 10 illustrates various detailed views of the nest as shown in FIGS. 1-6 component removal tool in accordance with the embodiment shown in FIG. 7;

DETAILED DESCRIPTION OF THE INVENTION

Figure 28:
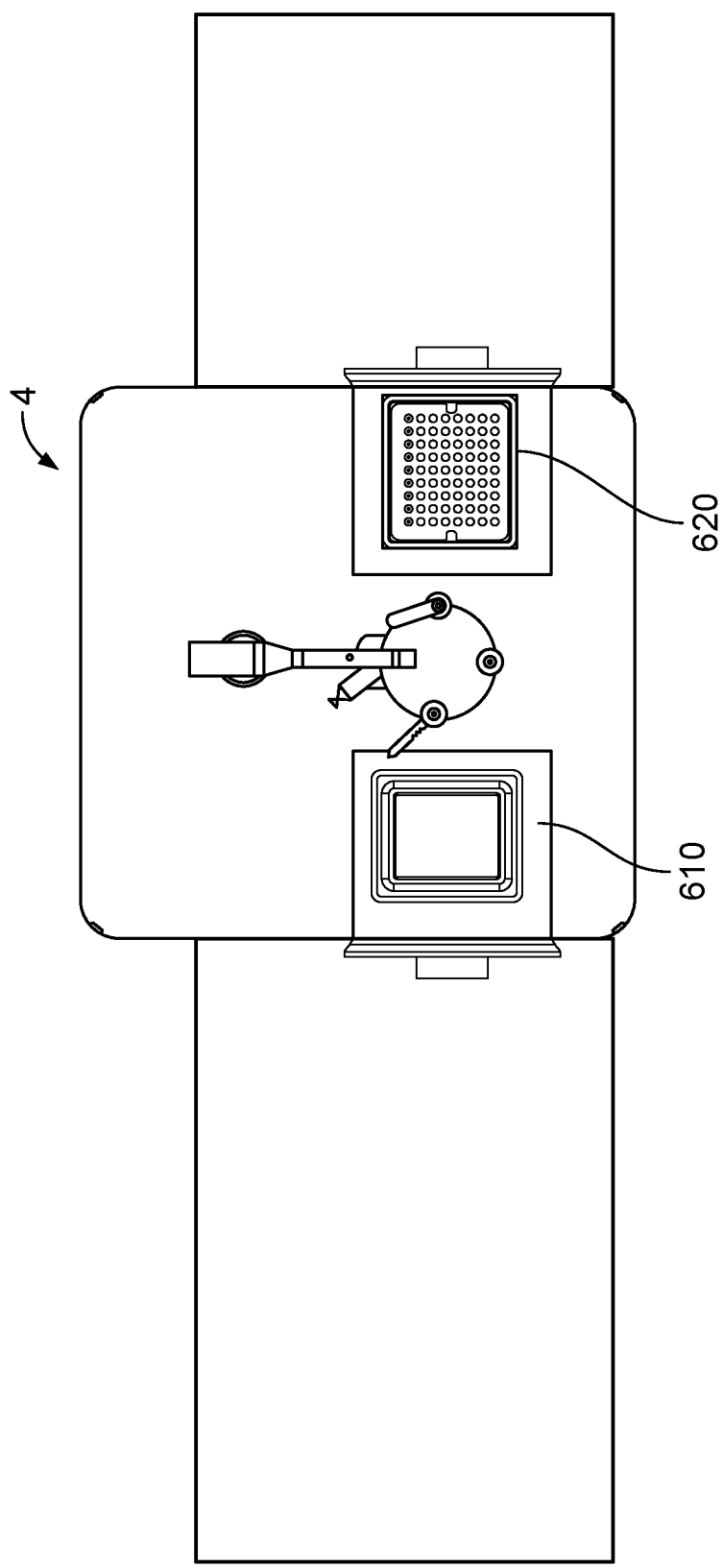
FIG. 28 illustrates a top view of an exemplary machine configured to assemble items provided in various of the aforementioned trays, the machine being illustrative of various concepts of the present invention.

It is well understood that in the field of medical devices that maintaining sterility during an assembly process is absolutely essential to maintaining the integrity of the final medical device. In the field of auto-injectors as well as other medical devices the specific parts of a device can be extremely small or delicate, as such the assembly is often achieved through robots having particular functions and a plurality of parts are precisely located at predetermined positions within the ISO-tub, as illustrated by FIG. 28 having robot 4 and receiving bays 610 or assembly bays 620 where assembled products can be placed. It will be appreciated that a particular station can have numerous robots and receiving bays configured to manipulate and/or assemble numerous parts of a given product.

FIGS. 1-6 illustrate a component storage and nesting system 10 after a first embodiment which includes an ISO-tray or tub 20 which is configured to be received by an exemplary receiving bay for later access by a particular robot. The tub 20 can be provided with varying dimensions which can aid in ensuring the proper placement of one or more components of a medical device 300 being contained therein.

As illustrated the particular component shown herein is a cannula and a lower vial assembly of an auto-injector which is configured to receive a dry powder or a liquid medicament which can later be lyophilized so as to provide a dry medicament cake for later reconstitution by the auto-injector in an actuation and mixing process prior to delivery. This particular component is merely for exemplary purposes but illustrates various aspects of the present invention which will be discussed in detail below. It will also be appreciated that the nest 100 can sit within the tub 20 and be sealed with a membrane 24, such as a Tyvek™ film, about an upper edge of the tub so as to protect the components 300 during storage and transport so as to minimize contamination.

In particular, the cannula and lower vial assembly includes a vial portion which is open at one end opposing the cannula. Since the vial is open it is preferred, in one embodiment, that the storage and placement of said vial into the nest 100 be done in an inverted fashion to prevent, and/or limit contamination from settling into the vial. However, the assembly must be righted or placed with the open end facing up so as to properly receive a powder or liquid being provided therein. The component 300 is received in one or more receptacles 104 provided within the nest 100. In some instances, the nest can be configured to be mirrored about a center line such that regardless of orientation, the receptacles 104 are properly aligned with respect to the tub 20 even if rotated 180 degrees, or 90 degrees, either when placing the nest in the tub 20 or when placing the tub into the receiving bay of the robotic station.

The receptacles can include a bottom portion 120 defining a lower limit of the placement of the particular component 300 as well as one or more retention clips 110 which maintain the position of the component within the receptacle 104.

A pickup tool 200 can then be provided to a user or a robot which is configured to have release mechanisms which disengage the retention clips 110 and grasp the component 300 when pressed into the receptacle, thus allowing the pickup tool to extract a particular component from a particular receptacle and then perform additional filling or assembly steps on that particular component.

In one embodiment, for this particular cannula assembly and vial component, the open end of the vial can then be flipped such that the open end is facing upward for a filling function.

It will also be appreciated that the reduction of robotic movements can result in faster assembly times and reduced robot cost In this manner, it will be appreciated that instead of inserting the tub 20 into the receiving bay of the workstation, that instead the nest 100 can be removed from the tub and the nest inverted and placed into the receiving bay so as to eliminate the need of the robot to perform the flipping step for filling.

Figure 1:
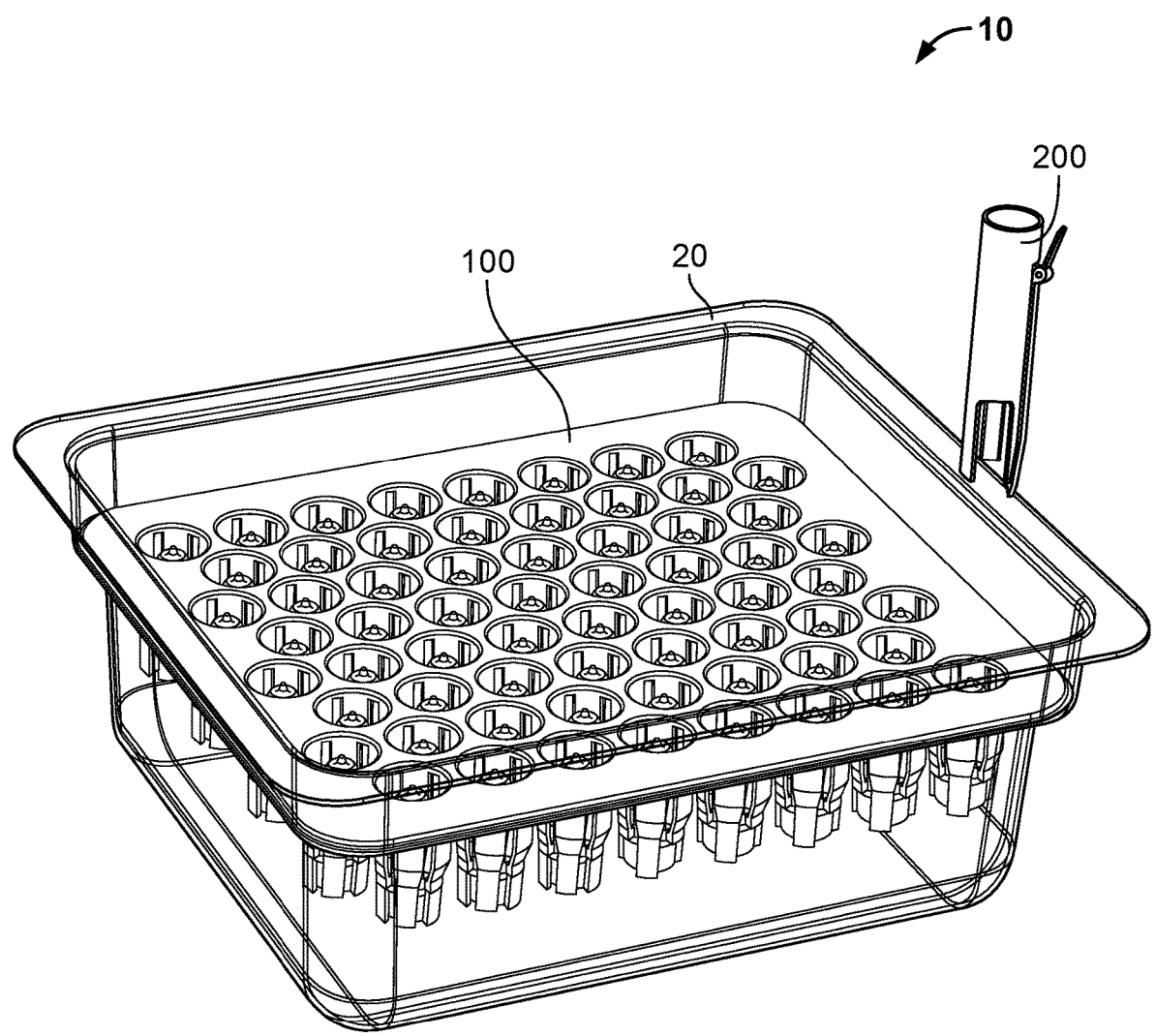
FIG. 1 illustrates a first embodiment of a component storage and nest system configured to be utilized in various steps of assembling an auto-injector in accordance with various aspects of the present invention.
Figure 2A:
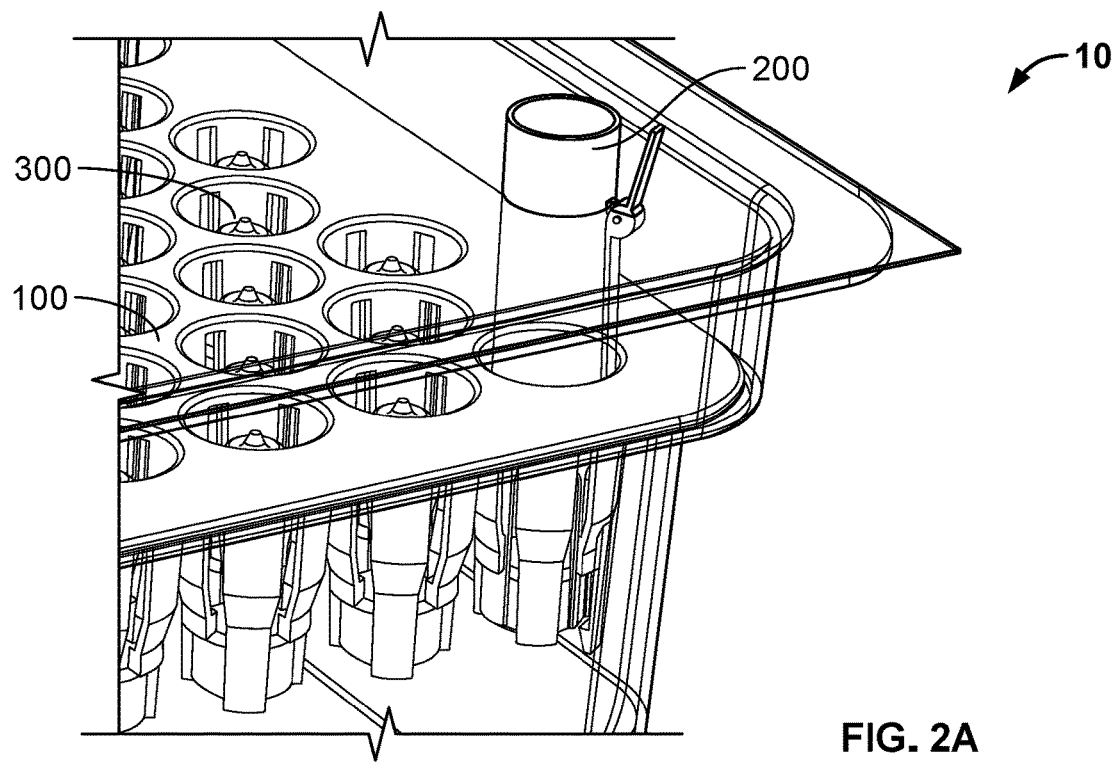
FIGS. 2A-B illustrate perspective views of the component storage and nesting system in addition with a component removal tool configured to remove one or more components from the storage and nest system.
Figure 2B:
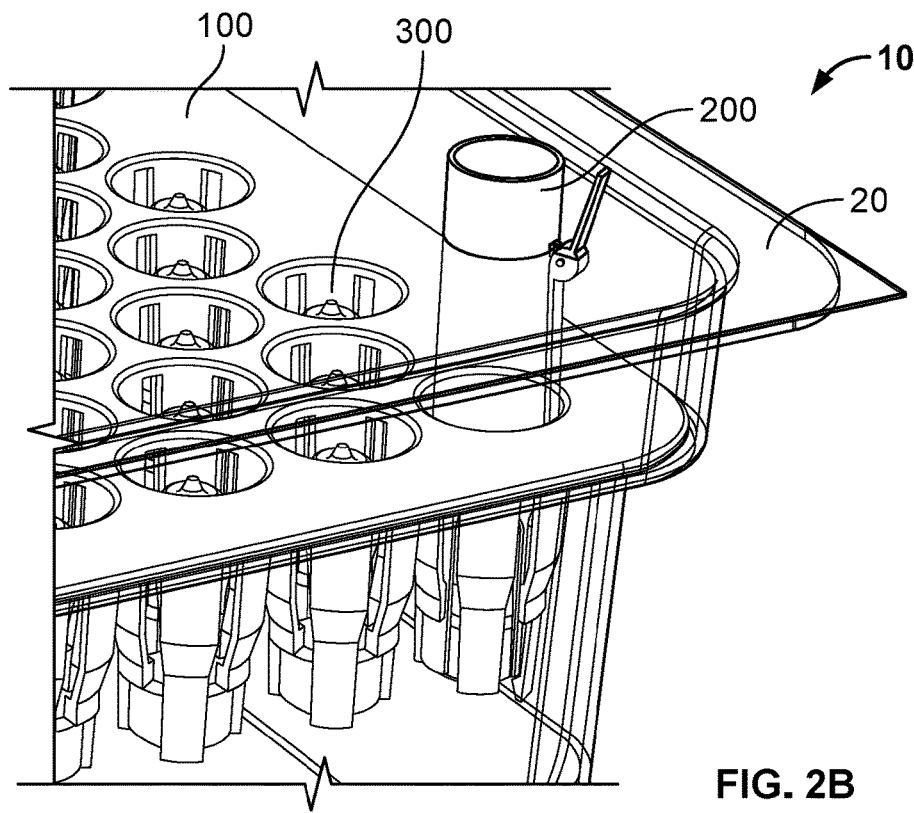
Figure 3:
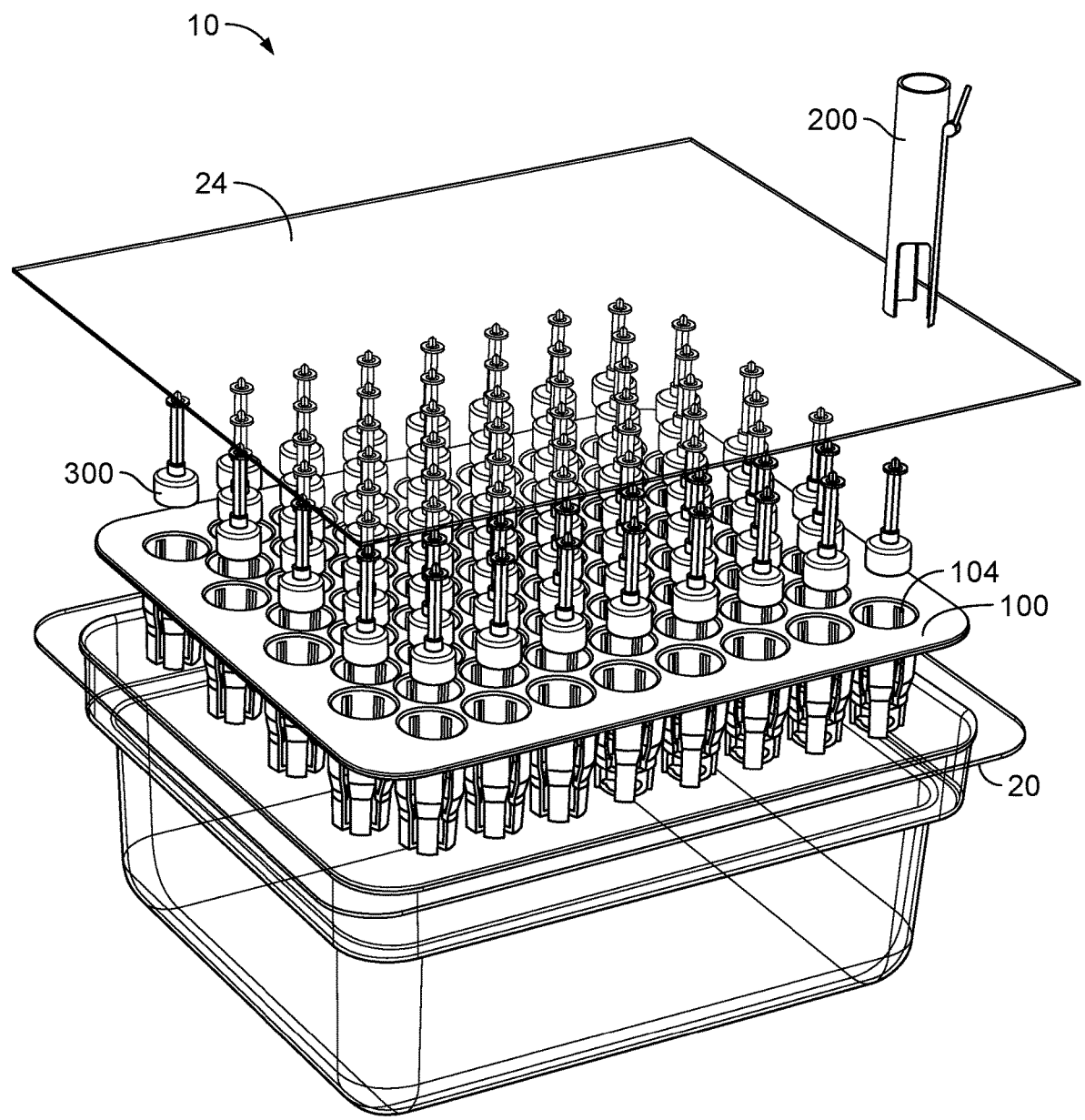
FIG. 3 illustrates an exploded perspective view of the component storage and nest system as well as the component removal tool.
Figure 4:
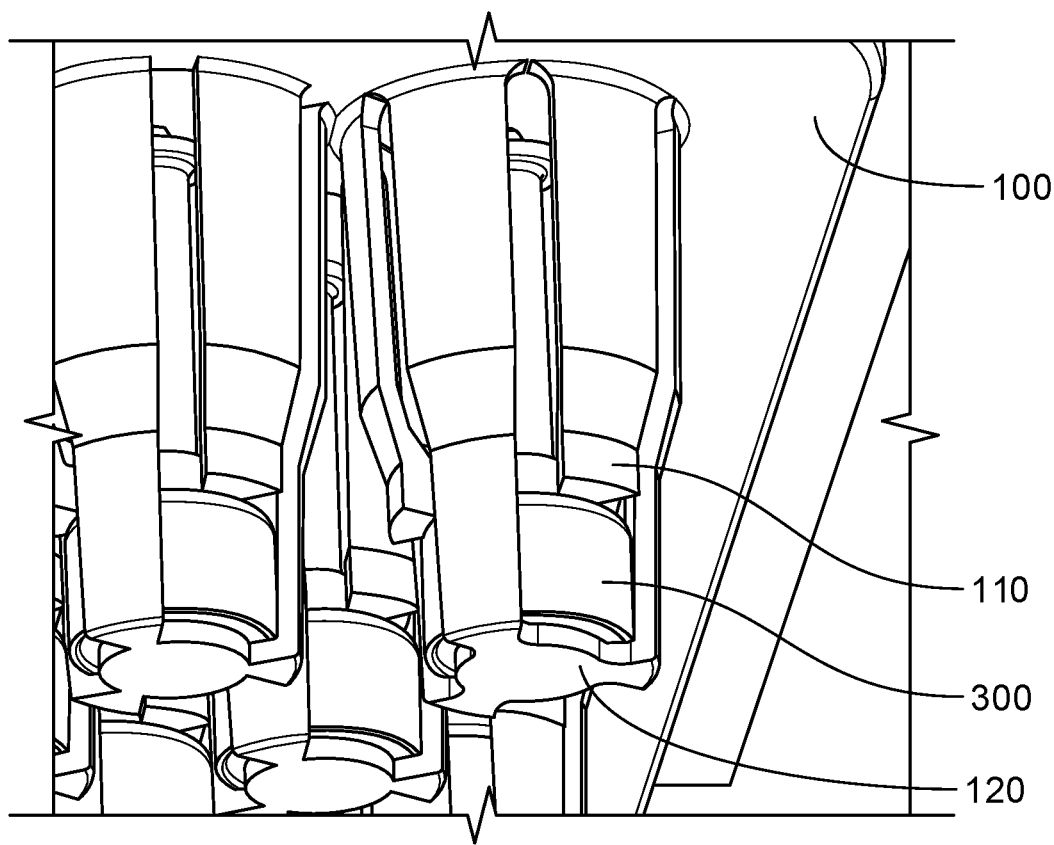
FIG. 4 illustrates a zoomed-in perspective view of nest portion of the component storage and nest system with an associated component provided therein.
Figure 5:
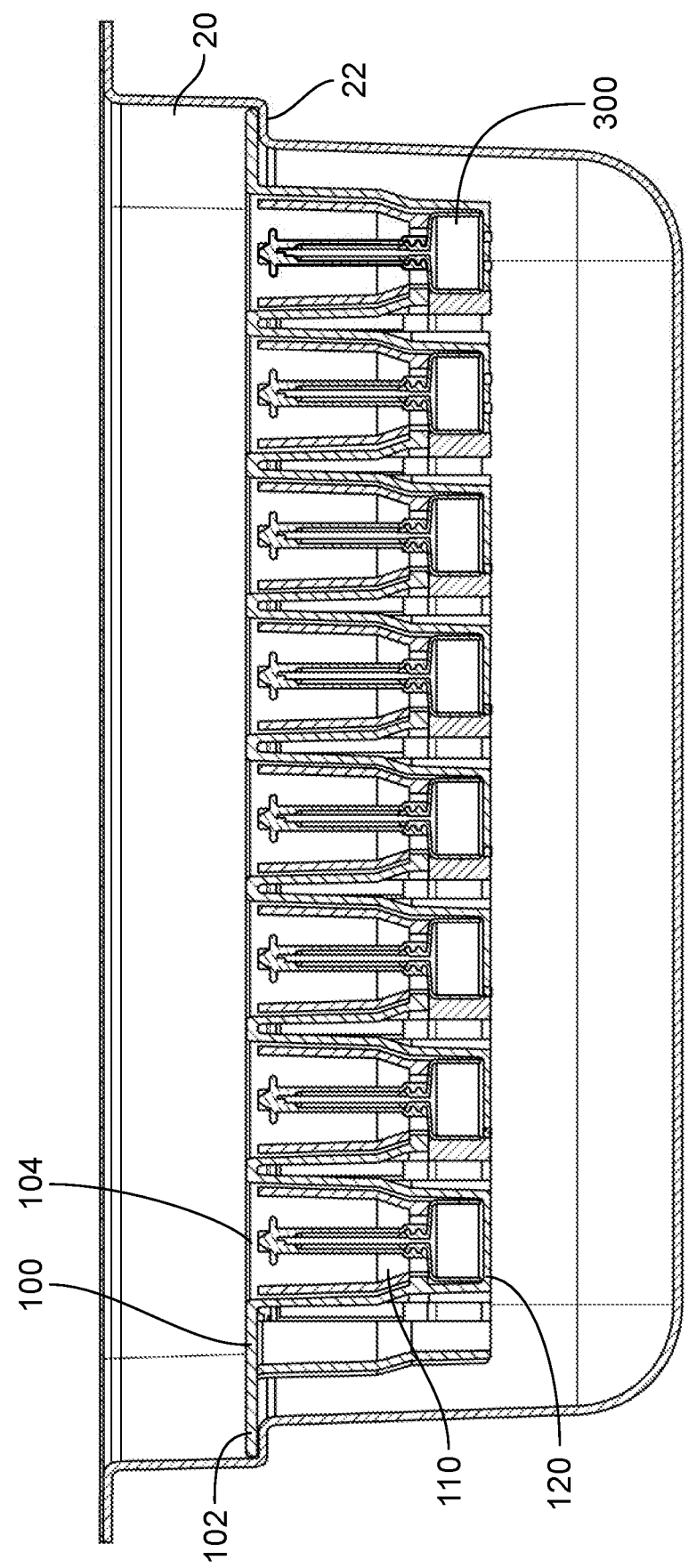
FIG. 5 illustrates a side partially transparent or cross-sectional view of the component storage and nest system in accordance with the embodiment shown in FIG. 3.
Figure 6:
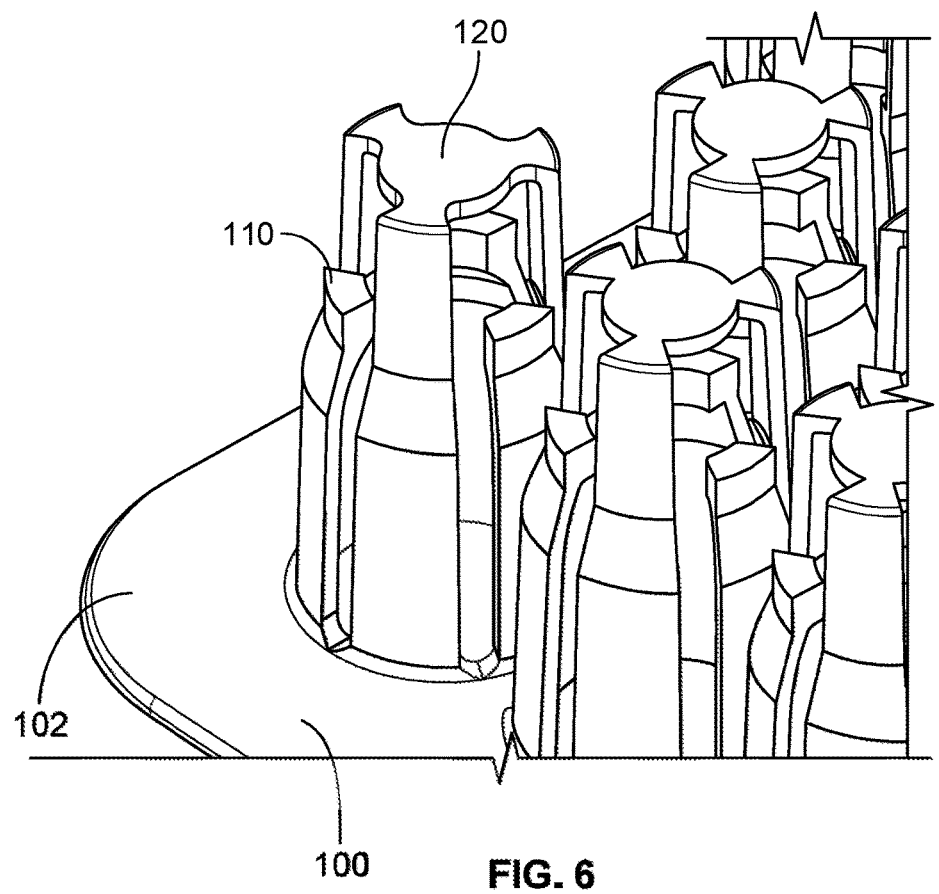
FIG. 6 illustrates a zoomed-in perspective view of a nest portion of the component storage and nest system.
Figure 7:
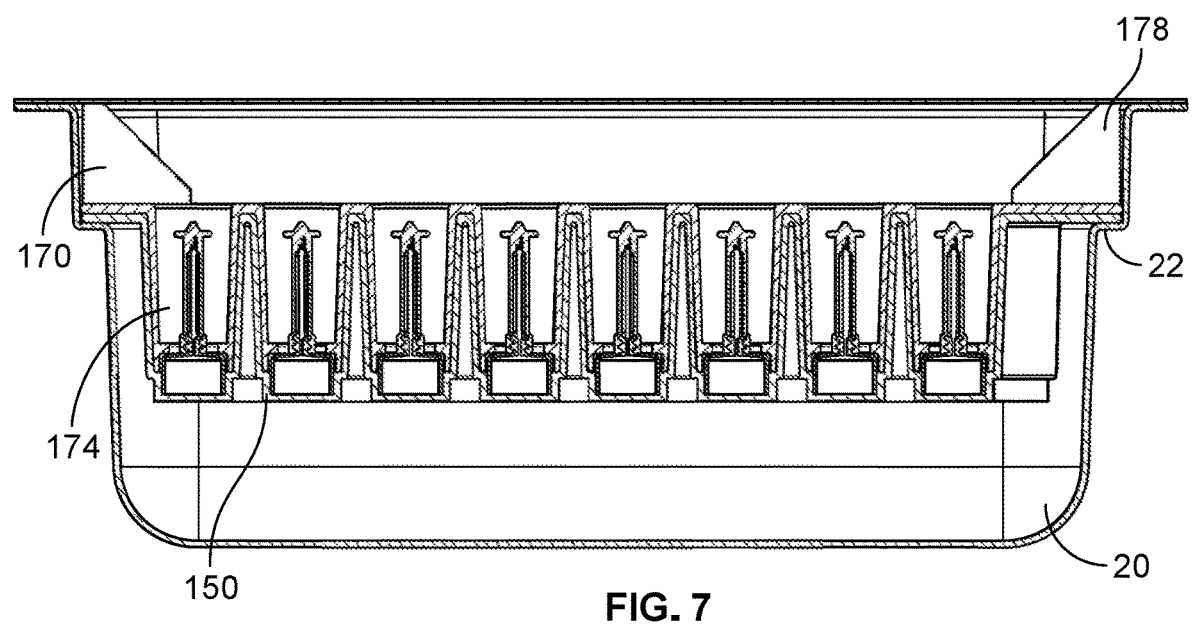
FIG. 7 illustrates a side partially transparent or cross-sectional view of the component storage and nest system and method utilizing an alternative nest portion.
Figure 8:
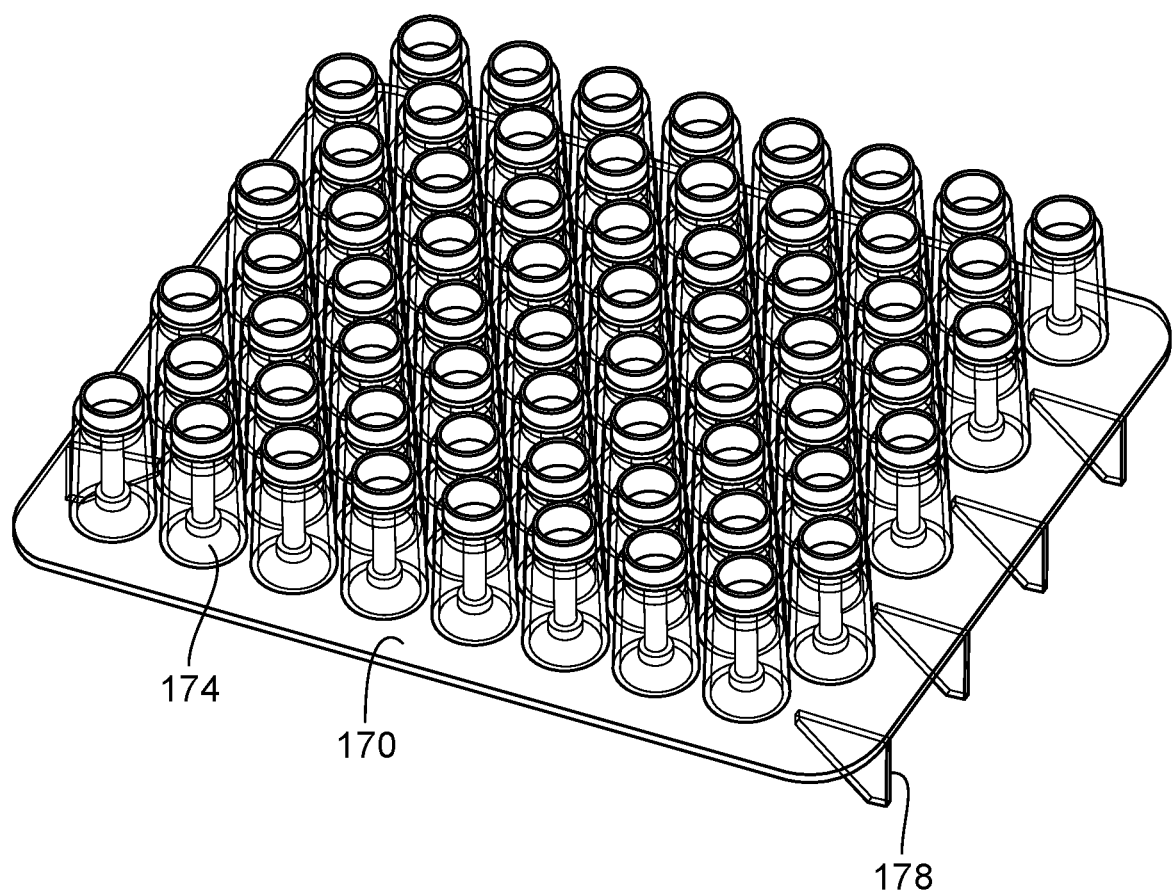
FIG. 8 illustrates a perspective view of the nest portion of the component storage and nest system of FIG. 7.
Figure 9:
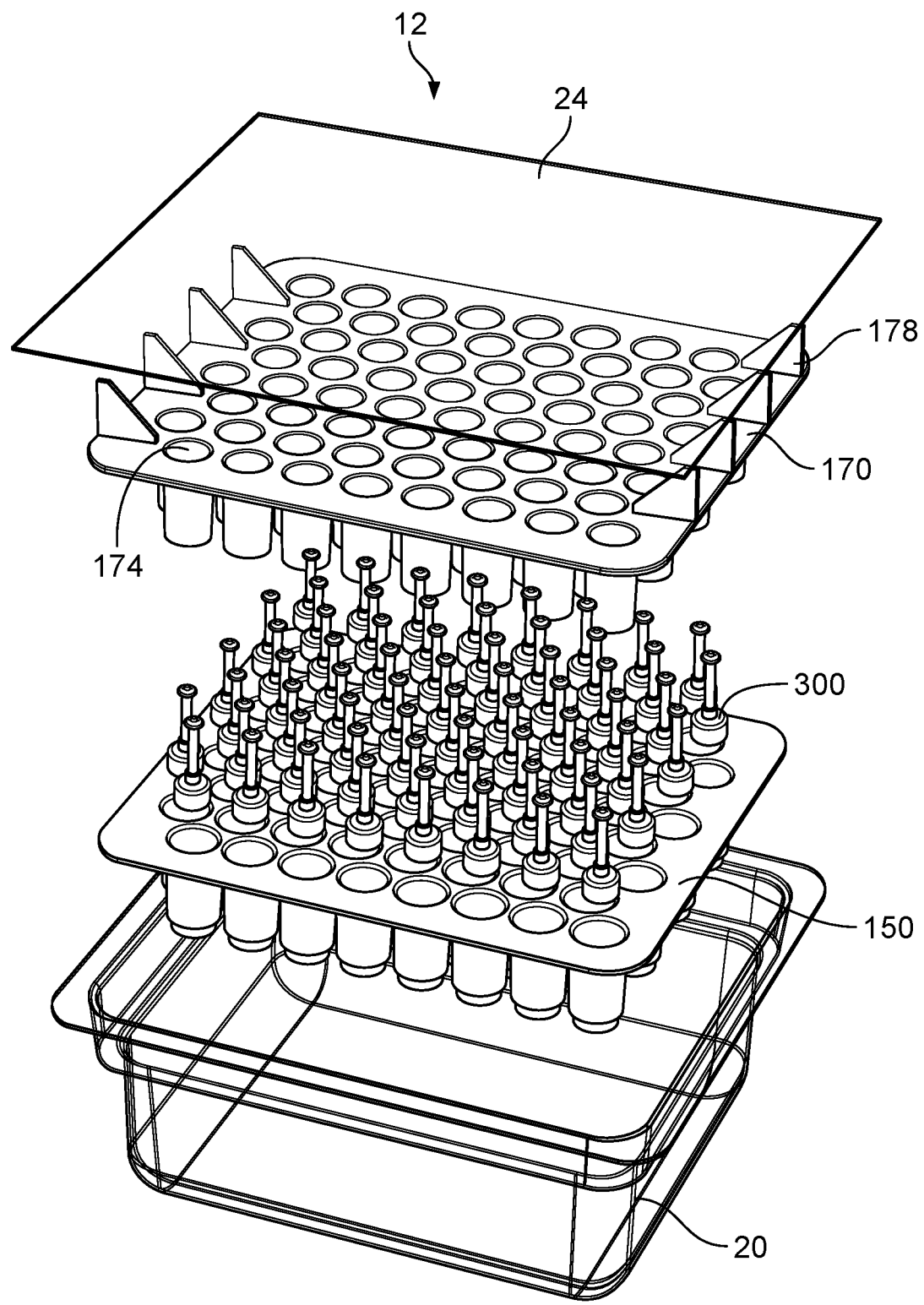
FIG. 9 illustrates an exploded perspective view of the component storage and nest system as well as the component removal tool in accordance with the embodiment shown in FIG. 7.

FIGS. 7-9 illustrate an alternative nest 150 which also rests on a lip 22 within a tub 20. However, the alternative nest 150 can include a nest having receptacles lacking a retention feature, but instead utilizes a secondary retainer nest which includes a plurality of pedestals or posts 174 which can press into the receptacles and hold the components 300. The secondary retainer nest 170 can include a plurality of feet 178 which extend from an upper surface and when flipped act as feet to properly align the top of each post or pedestal 174 with respect to the robot. This assembly 12 can be utilized by removing the nest 150 and the secondary retainer nest 170 from the tub 20 together. The nest 150 and retainer nest 170 can be flipped, and then the nest 150 removed such that each of the components 300 are supported by the individual pedestals 174 and the retainer nest is supported by the extensions or feet 178, as shown in FIG. 8. Then each of the components 300 are properly oriented for a filling step or function without the need for a robotic movement of flipping each component would have been needed for such.

This also enables a robot or operator to "de-nest" in a standard way (as state-of-the-art prefilled syringes (PFS) are preferably de-nested from the side, as to not hover over the drug fill portion of the PFS) in the event that filling must be done with the drug container out of the nest.

In another embodiment, the retainer nest 170 can be removed from assembly 12 leaving nest 150 along with components 300 behind inside the tub 20. A pick-and-place tool can come in and grab each of the components without first requiring the de-engagement of any retention clips 110 as described in nest 100.

Figure 11:
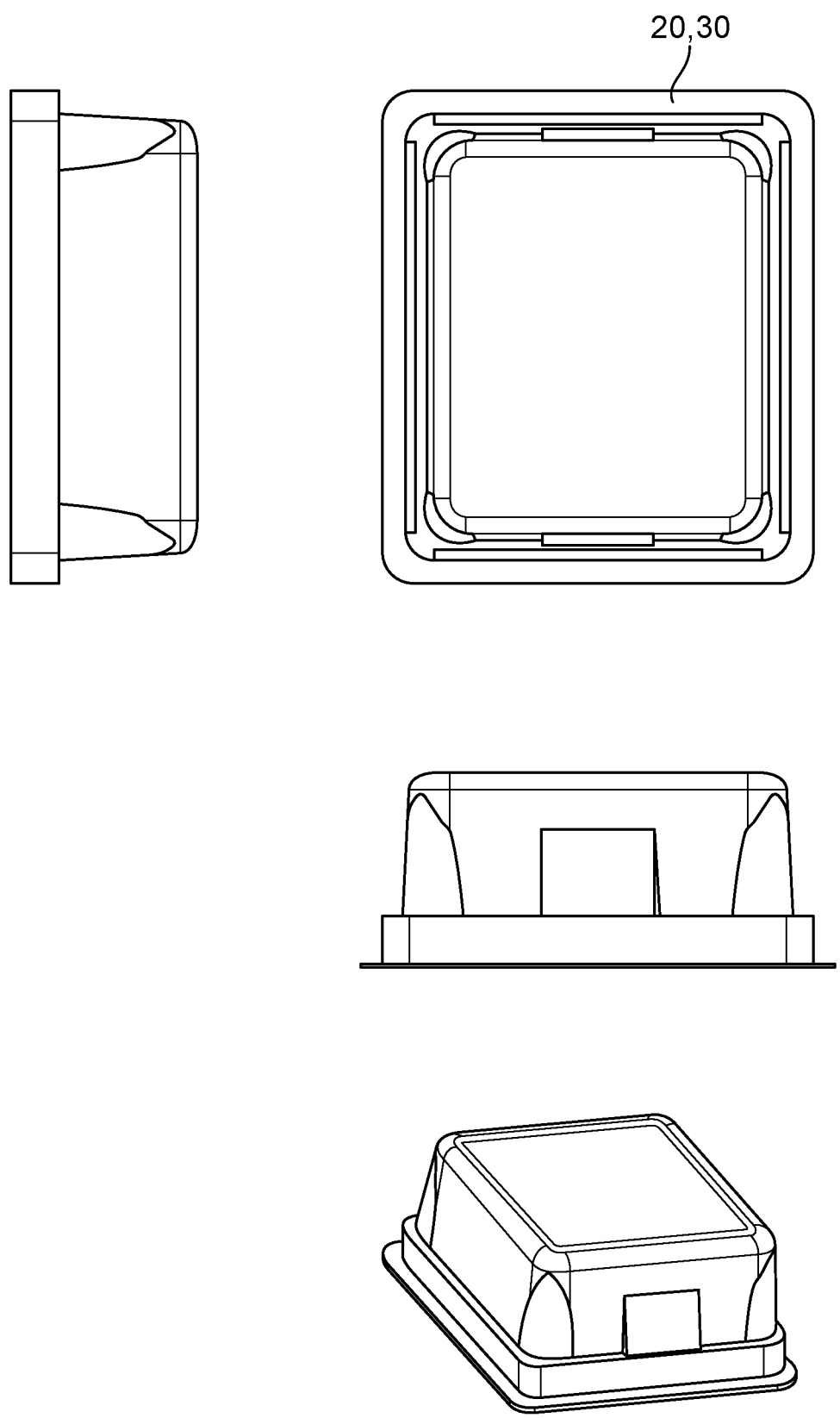
FIG. 11 illustrates various detailed views of an exterior tub portion for use in one or more of the various embodiments shown herein.
Figure 12:
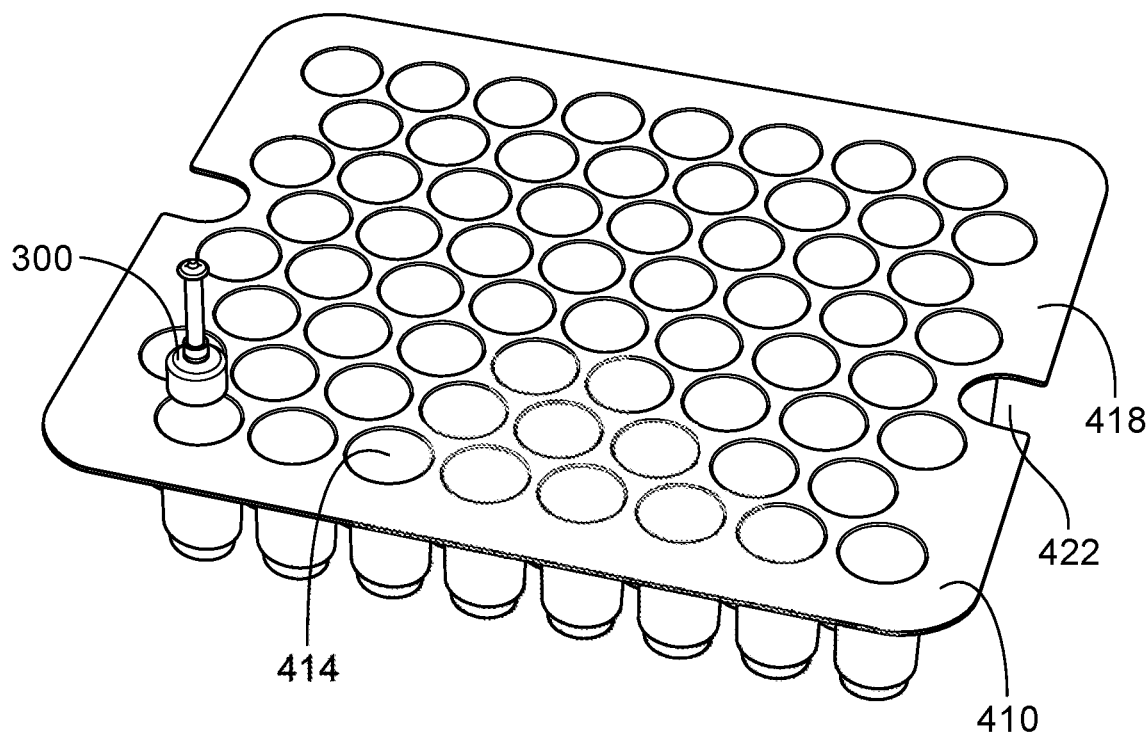
FIG. 12 illustrates various detailed views of yet another exemplary primary nest for use in a flush multi-nest component storage and nesting system.
Figure 13:
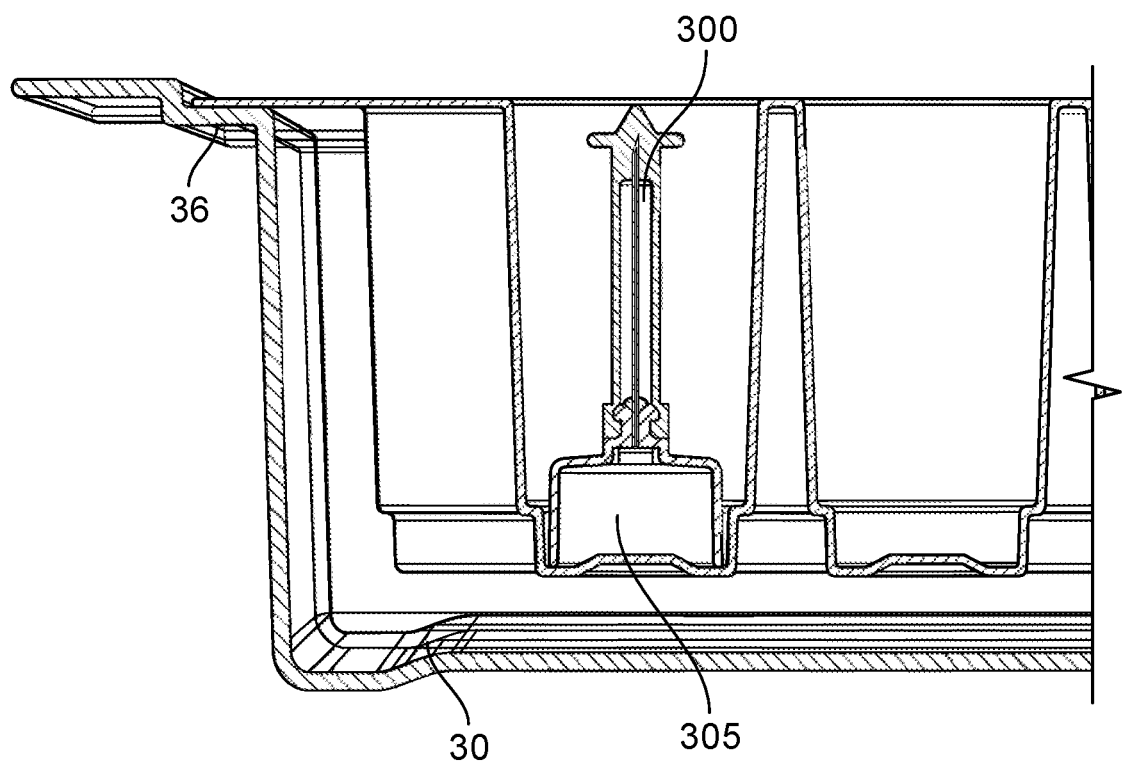
FIG. 13 illustrates a side cross-sectional view of a flush multi-nest component storage and nesting system utilizing the primary nest of FIG. 12 having a component of the auto-injector contained therein.
Figure 14:
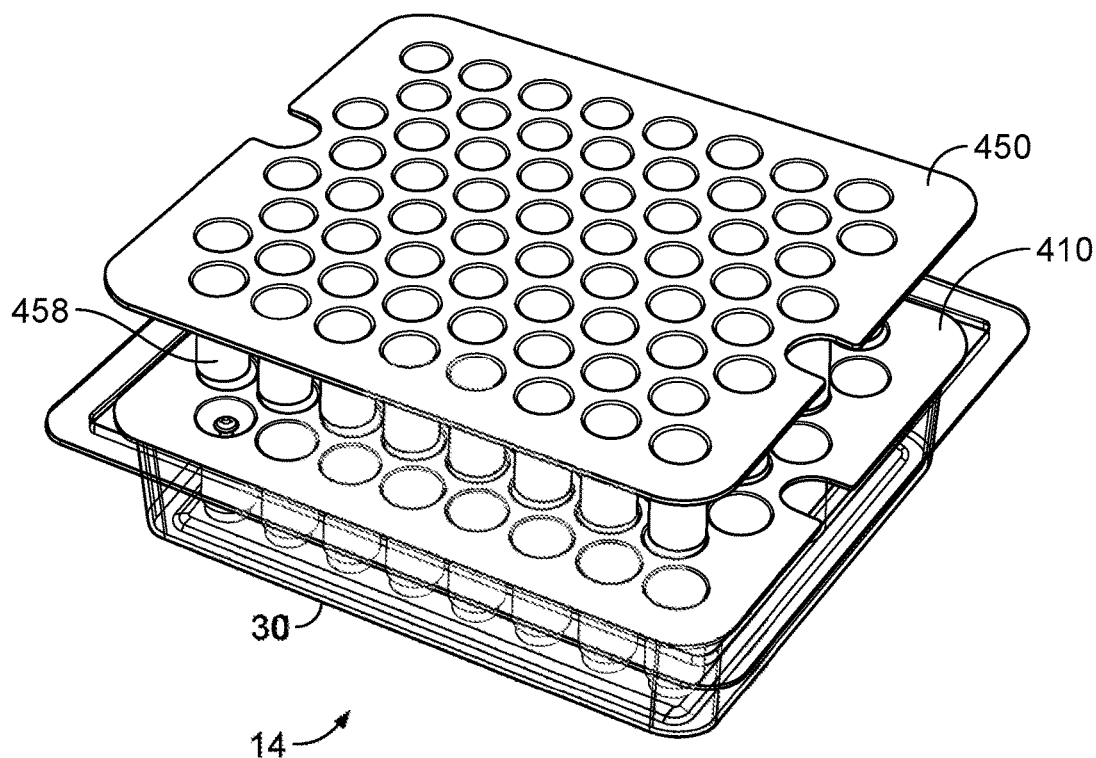
FIG. 14 illustrates a perspective exploded view of the flush multi-nest component storage and nesting system of FIG. 13 prior to insertion of a secondary or retainer nest.

FIGS. 10 and 11 illustrate detailed views of both nests and tubs adaptable for use in the various embodiments disclosed herein, namely FIG. 10 illustrates the orientation of each receptacle and how regardless of placement within the tub, the specific arrangement of the receptacles will be the same even when flipped 180 degrees.

FIGS. 12-19 illustrate an alternative storage assembly and arrangement 14 with a tub 30 having a shorter depth such that the primary nest 410 and the retainer nest 450 are flush with an upper surface when placed within the tub 30. It will be appreciated that the flange portion 36 has a proper depth so as to coincide with the stacked depth of the flange portions of the primary nest 410 and the retainer nest 450.

It will also be appreciated that the primary nest or retainer nest can be provided with a cutout 422 which allows for a user or robotic handling and aids in separation from the respective tub. It will be appreciated that the cutout 422 can be sized or shaped so as to allow for manipulation by a human hand or by any desired robotic component.

Figure 15:
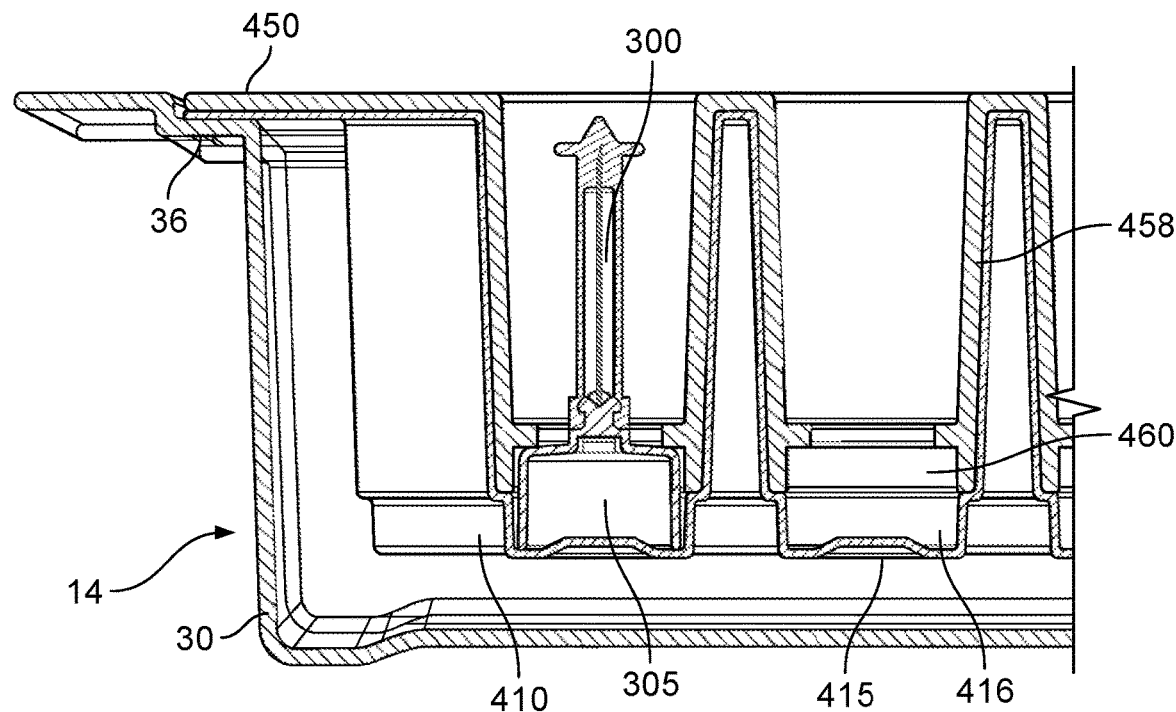
FIG. 15 illustrates a side cross-sectional view of a flush multi-nest component storage and nesting system utilizing the primary nest of FIG. 12 having secondary or retainer nest inserted therein.
Figure 16:
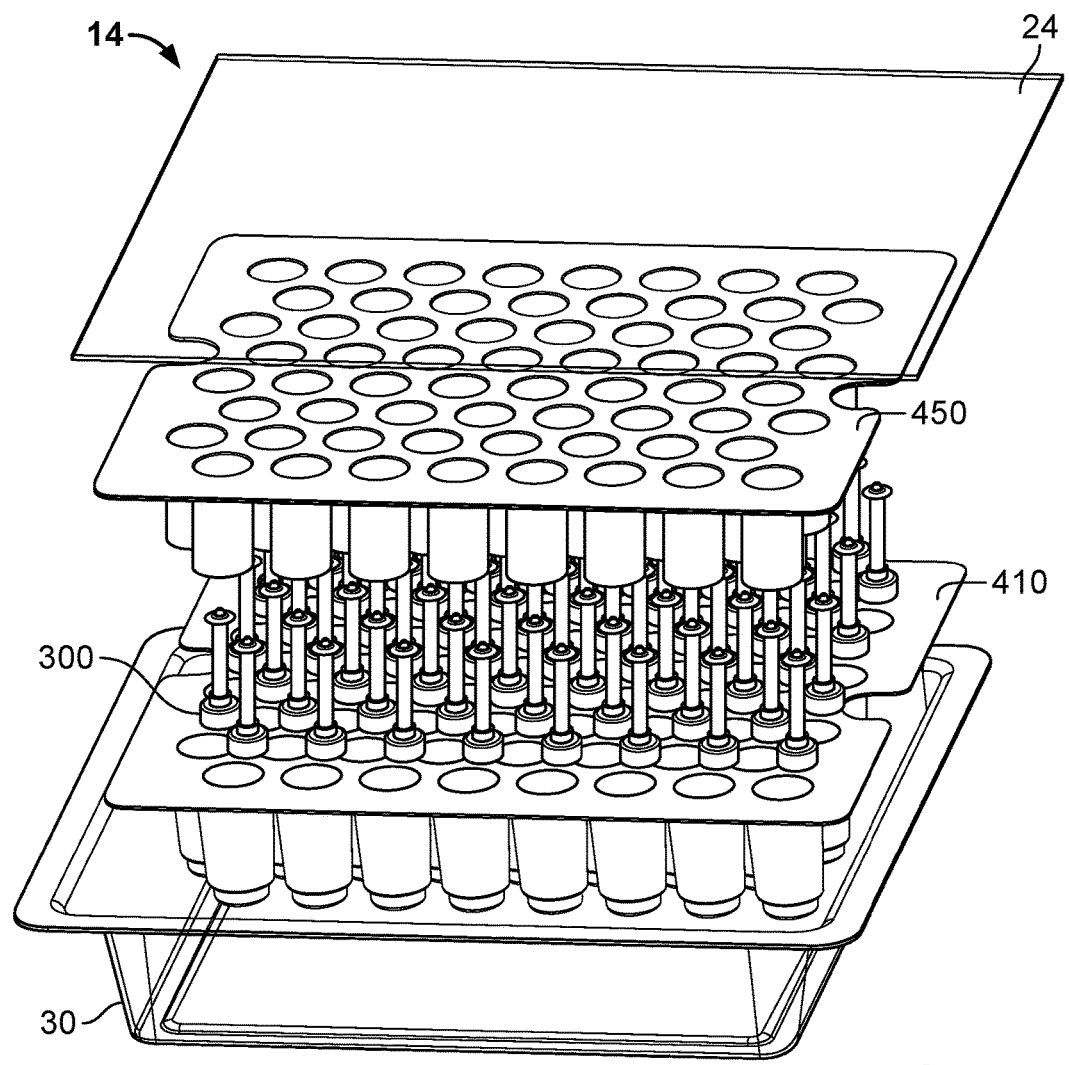
FIG. 16 illustrates a perspective exploded view of the complete flush multi-nest component storage and nesting system of FIG. 15.
Figure 17:
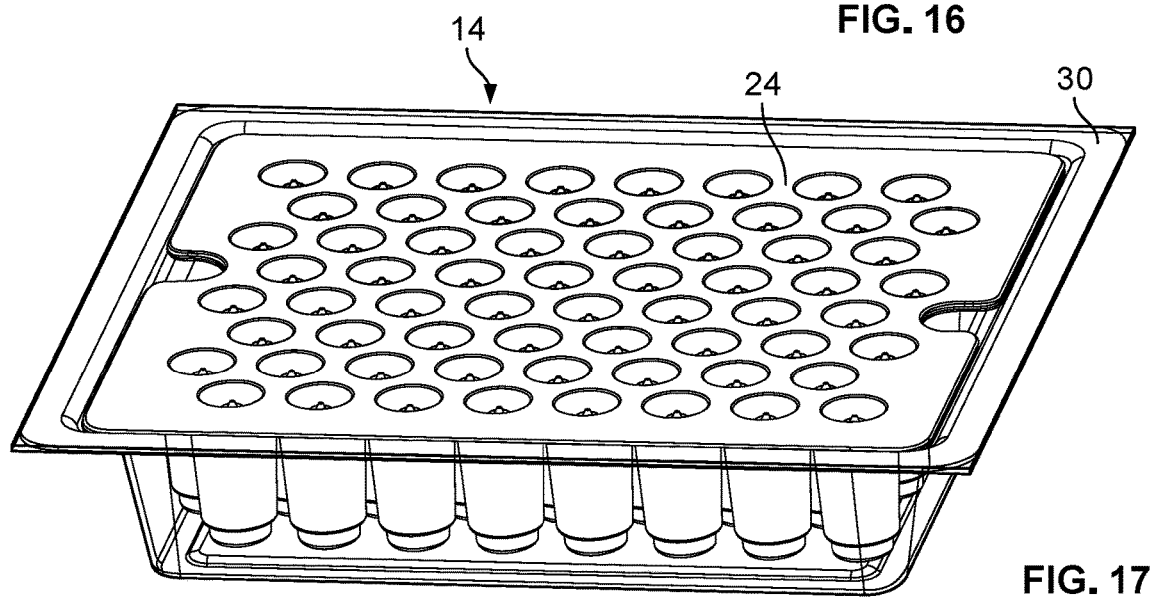
FIG. 17 illustrates a perspective assembled view of the flush multi-nest component storage and nesting system of FIG. 15 in a sealed configuration.
Figure 18A:
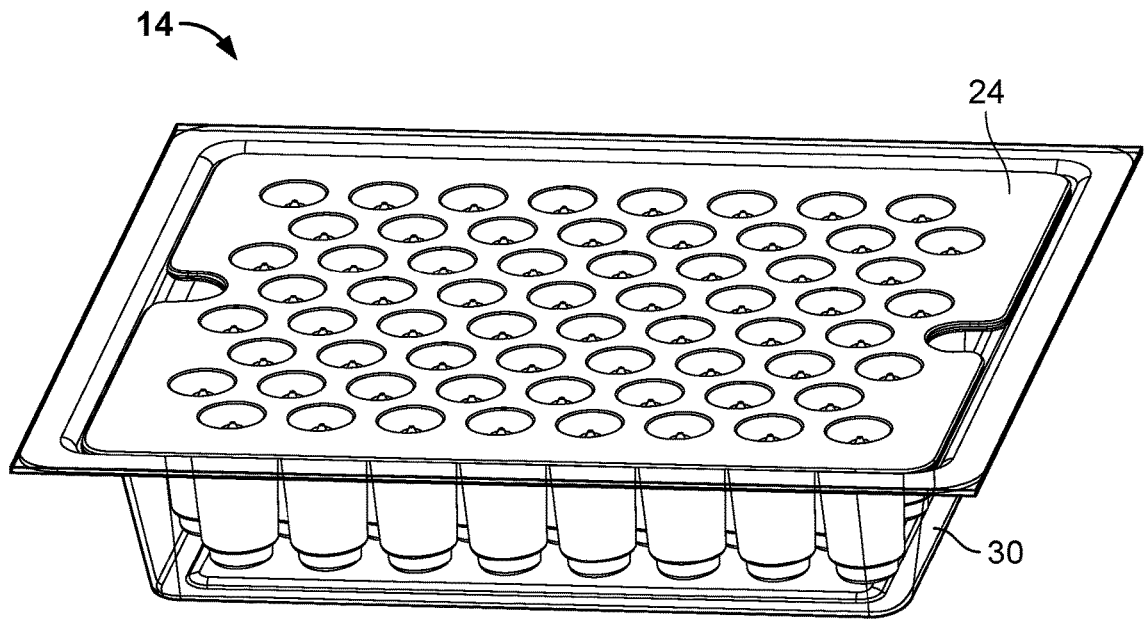
FIGS. 18A-C illustrate side perspective views of various stages of a component preparation method utilizing the FIG. 14 illustrates a perspective exploded view of the flush multi-nest component storage and nesting system of FIG. 13 prior to insertion of a secondary or retainer nest.
Figure 18B:
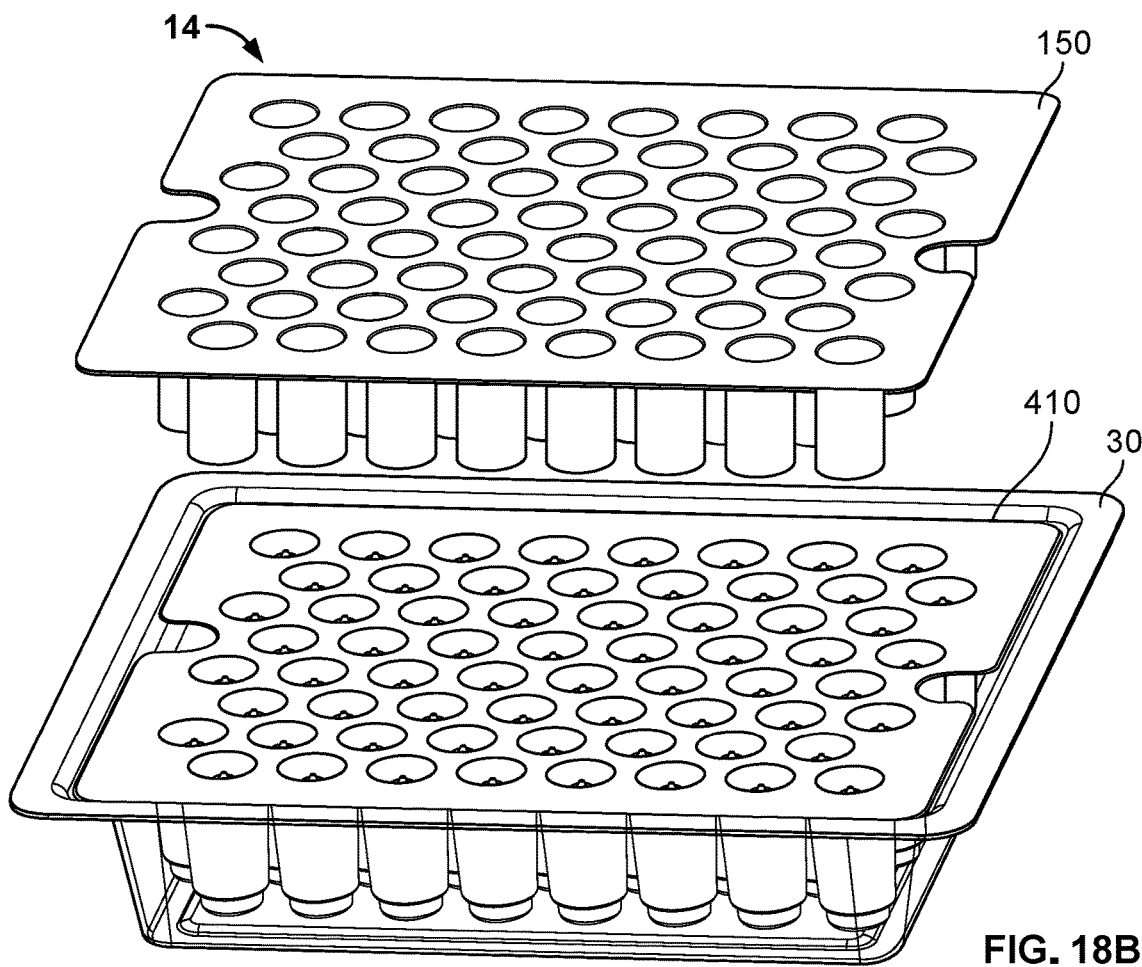
Figure 18C:
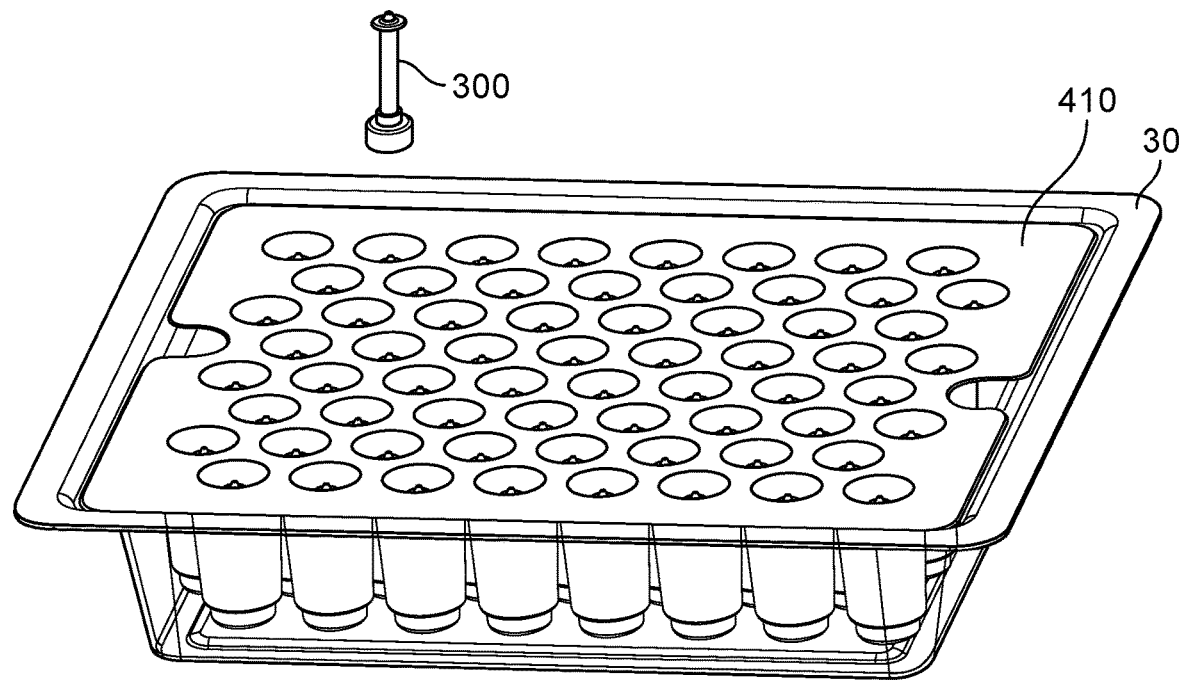

Looking in particular at FIG. 15, the pedestals or posts 458 of 450 have a flared end 460 that is configured to conform around the lower vial portion 305 of component 300 and help to maintain consistent relative position. This flared end 460 aligns with a receiving end 416 of the pedestal or post 414 of the lower nest 410. Both 460 and 416 conform and align concentrically. In some instances, a seal is formed between 460 and 416. Additionally, raised portion 415 is provided to help align to and be partially inserted into the open end of the lower vial 305 of component 300. In some versions apertures or holes are formed in the bottom portion of 414. In other embodiments, the raised portion 415 with angles side acts to direct any debris to the bottom of the interior of each pedestal or post 414.

Figure 19A:
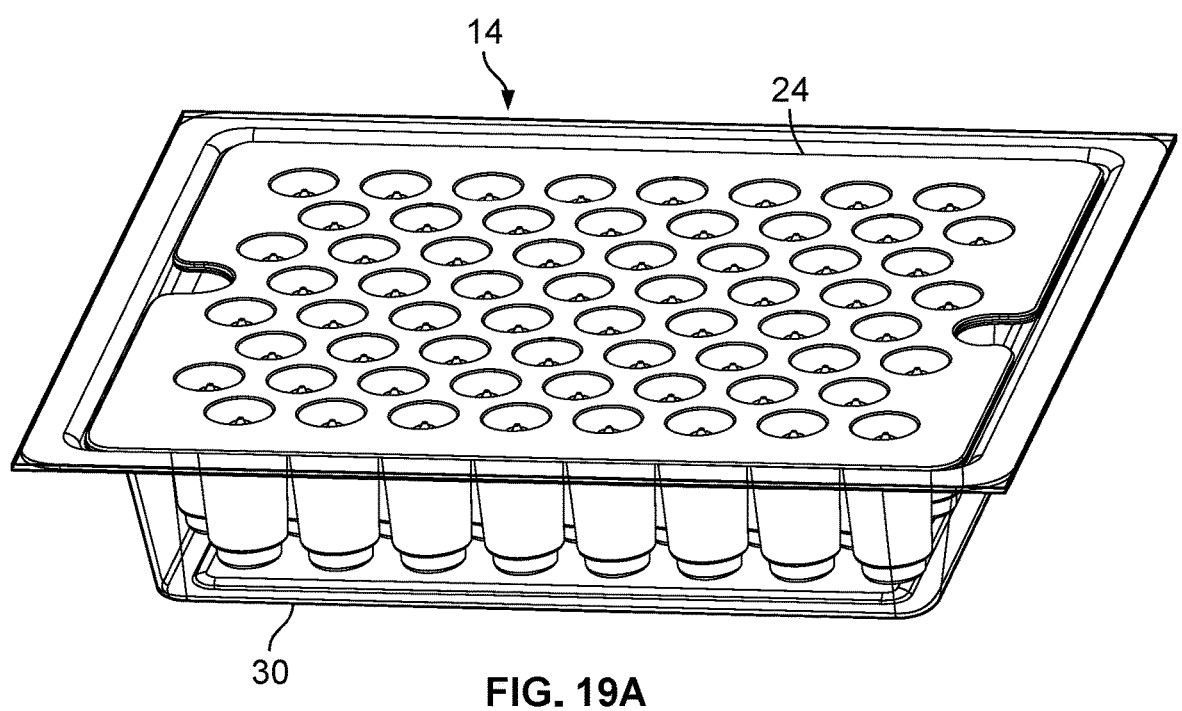
FIGS. 19A-C illustrate side perspective views of various stages of an alternative component preparation method utilizing the FIG. 14 illustrates a perspective exploded view of the flush multi-nest component storage and nesting system of FIG. 13 prior to insertion of a secondary or retainer nest.
Figure 19B:
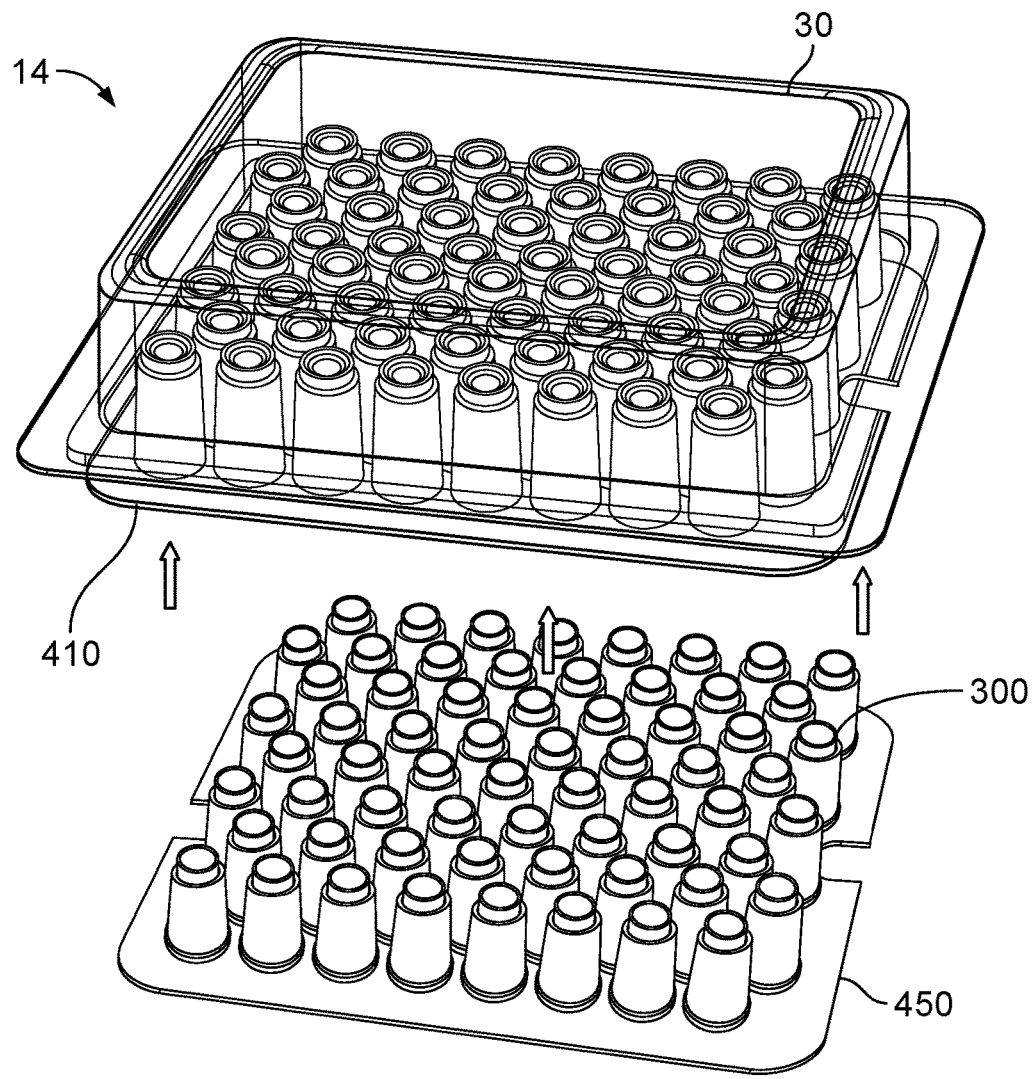
Figure 19C:
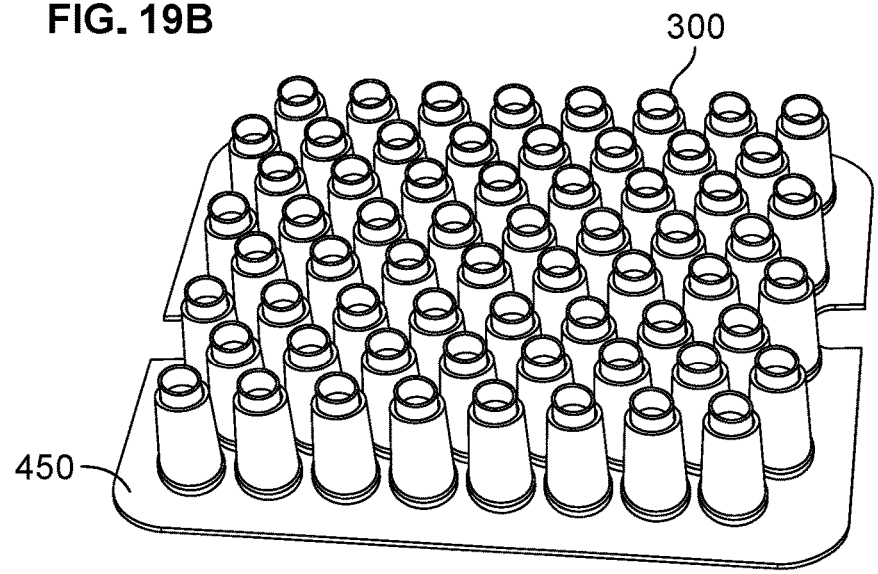
Figure 20:
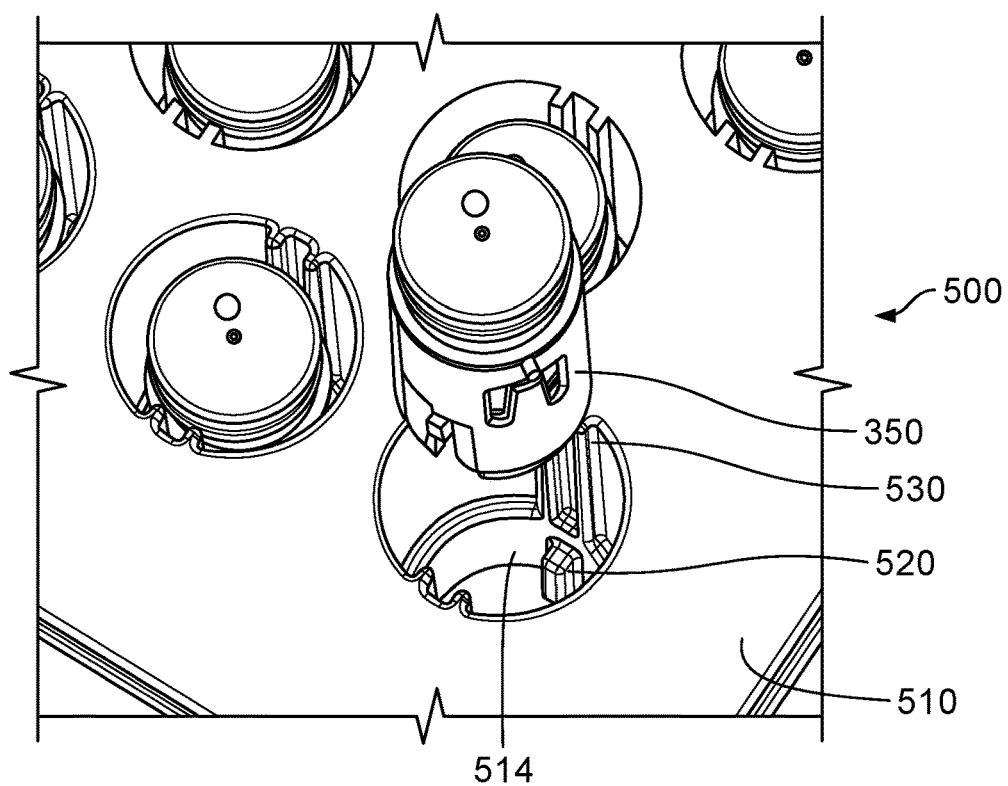
FIG. 20 illustrates yet another alternative nest for use with an alternative component of an auto-injector for the storage and preparation of the alternative component during an assembly procedure.
Figure 21:
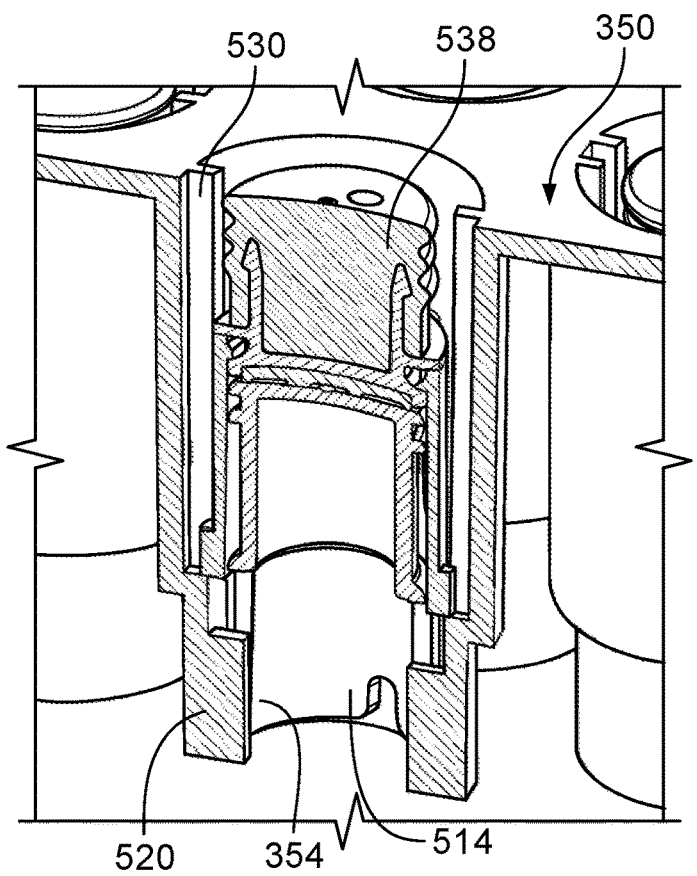
FIG. 21 illustrates a side cross-sectional view of the alternative nest and alternative component of FIG. 20.
Figure 22:
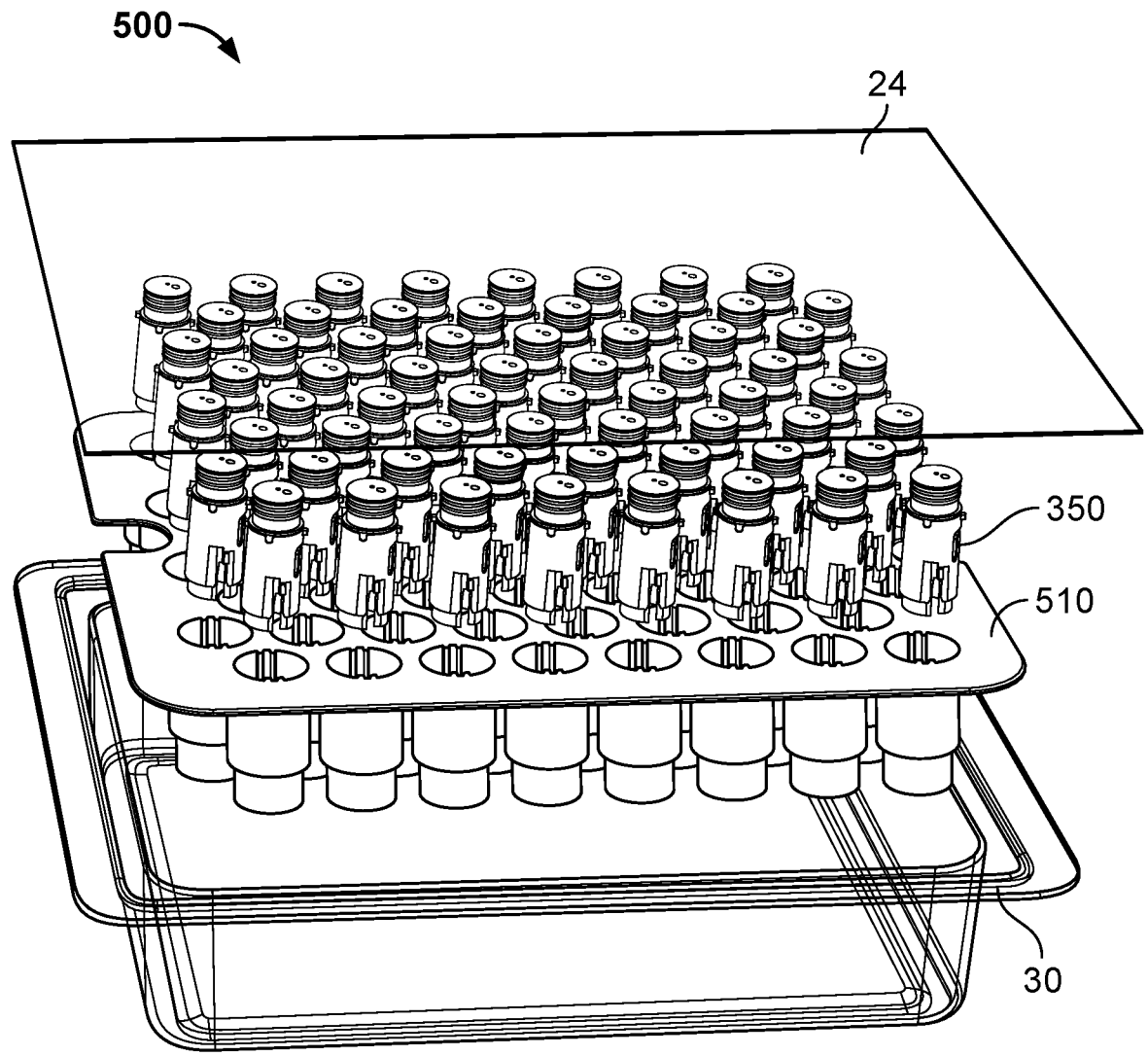
FIG. 22 illustrates an exploded perspective view of the alternative component and nest as utilized in an ISO tub.
Figure 23:
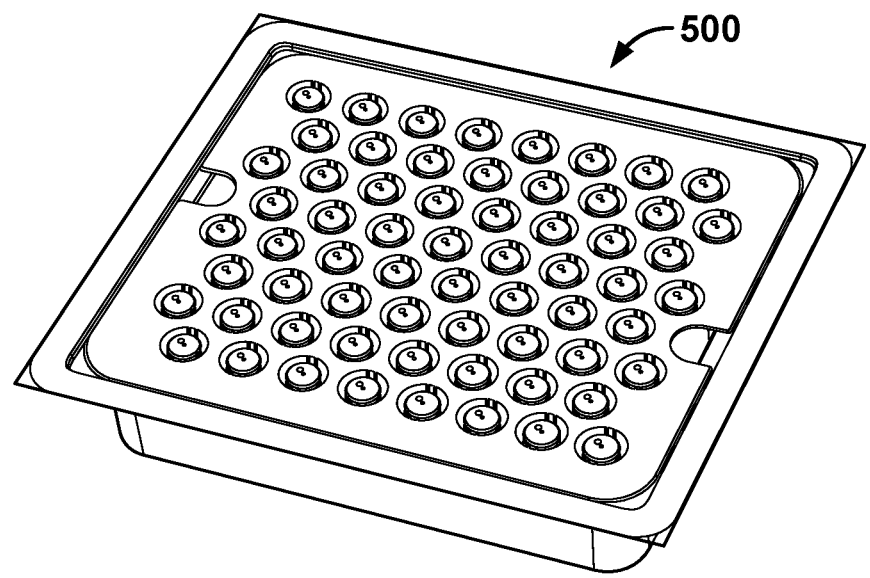
FIG. 23 illustrates an assembled perspective view of the assembly of FIG. 22.
Figure 24A:
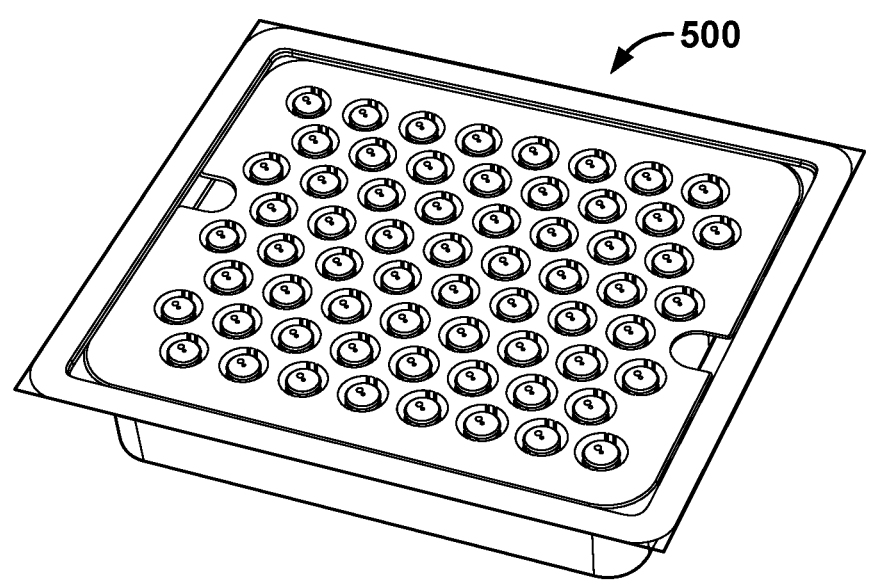
FIGS. 24A-C illustrate side perspective views of an exemplary preparation procedure for delivering the alternative nest of FIG. 20 to an assembly machine with a de-nesting tray illustrative of various concepts of the present invention.
Figure 24B:
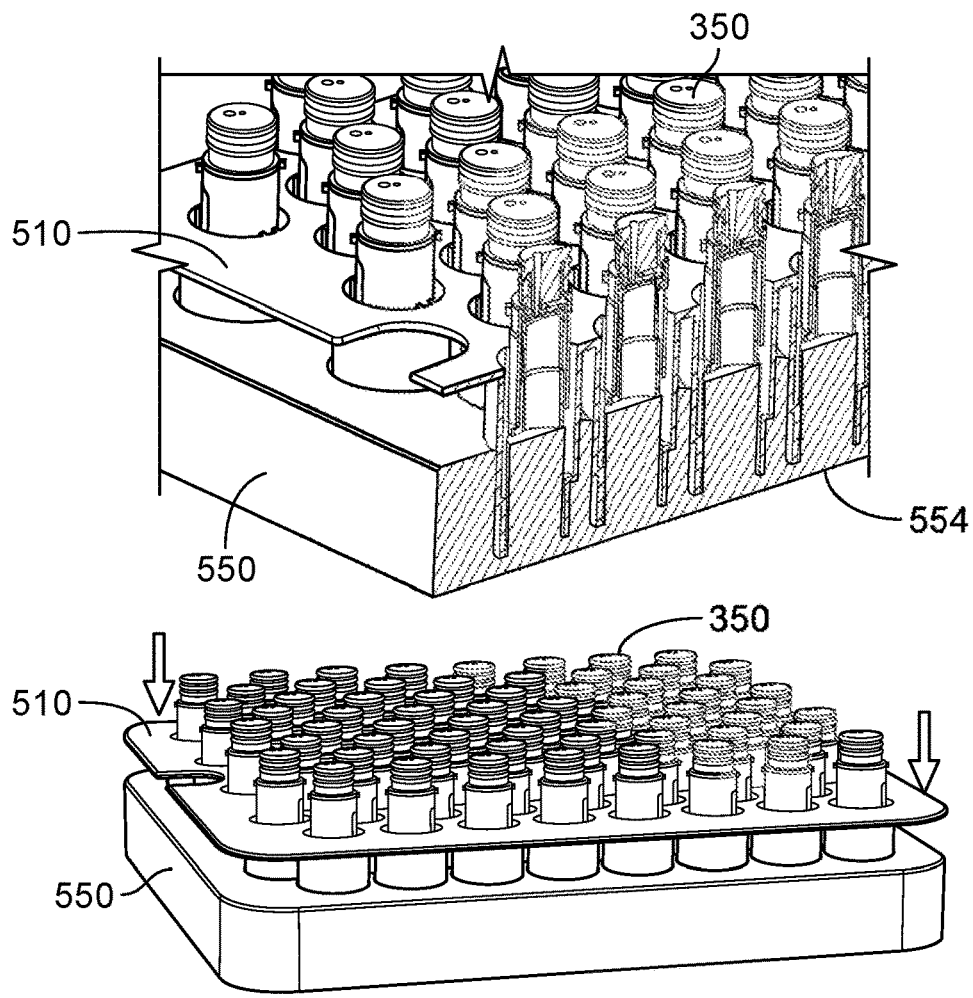
Figure 24C:
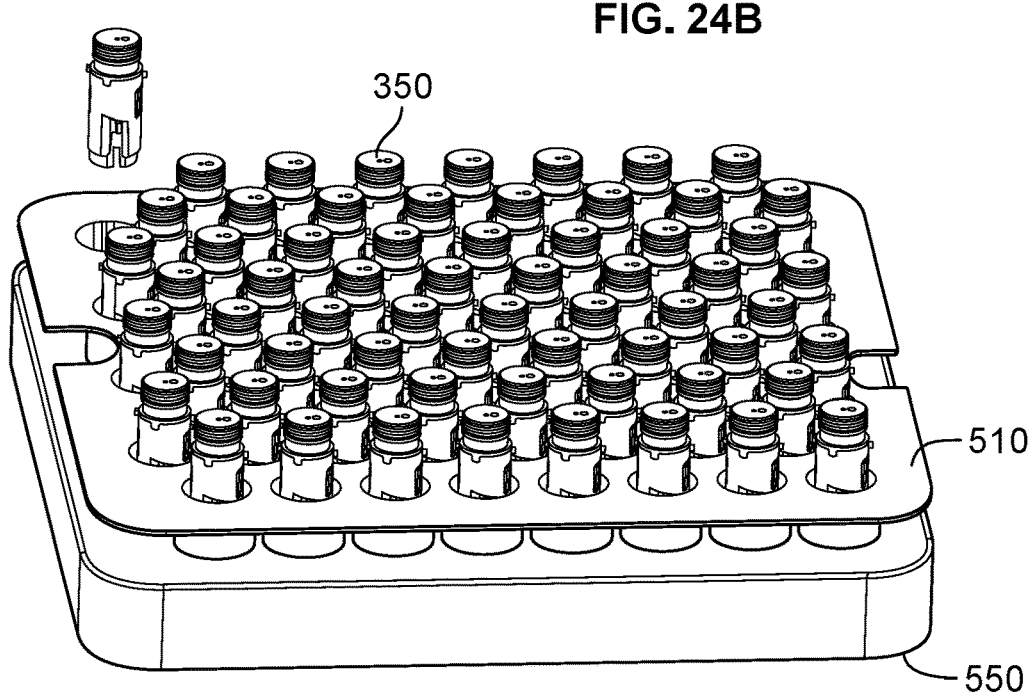

Similar to the embodiments discussed above, the process for using this embodiment can include the mere placement of the tub 30 into a receiving bay and the removal of the sealing membrane 24, wherein the secondary retainer nest 450 is removed and the components 300 are removed from the primary nest 410 and flipped individually. Alternatively, this storage assembly 14 can also be used by removing the sealing membrane 24, removing the primary nest 410 from the tub with the retainer nest 450, flipping the primary and secondary nests and removing the primary nest 410 to leave the secondary retainer nest 450 with the components 300 properly oriented thereon and placing that into the receiving bay of the working area. Further, this storage assembly 14 can also be used by removing the sealing membrane 24, flipping the tub with the nest and retainer nest therein, removing the tub 30 and the primary nest 410 to leave the secondary retainer nest 450 with the components 300 properly oriented thereon and placing that into the receiving bay of the working area as illustrated in FIGS. 19A-C.

FIGS. 20-24 illustrate an alternative nesting system 500 which is designed for use with an alternative component 350. In this illustrative example, the alternative component 350 includes a valve body with primary and secondary plungers for use with an end auto-injector illustrative of various aspects of the present invention. Being a valve body, it will be appreciated that the valve will include open and closed configurations wherein in the particular embodiment, the valve body includes a channel on a perimeter portion indicative of an open configuration. It will be appreciated that depending on the state of the components being provided in the vial of component 300 that various valve configurations will be desired. In the present illustration, a liquid containing a drug is being provided into the lower vial prior to installation of the valve assembly prior to lyophilization. As such, it is desired that the valve be open such that the liquid component can evaporate and escape through the valve, wherein the valve will be closed after lyophilization is complete. As such the secondary component nesting tray 510 can be provided with a plurality of receptacles 514 for receiving a valve assembly or secondary component 350. The receptacles 514 can include a plurality of configuration ensuring features, illustrated herein as ribs or channels 530 which, ensure proper alignment of each valve component, or any secondary component 350 wherein a particular orientation is important. A protrusion can then be provided on the perimeter of the second component 350 which slides into the channel 530 or otherwise engages the ribs and prevents misalignment after insertion. Further, the channel will accept corresponding protrusions provided on the medical component, wherein the channel can be configured to interfere with insertion when the various protrusions on the medical component are not properly aligned, thus indicating an incorrect valve position.

A status protrusion or boss 520 can then be provided on an interior surface of the receptacle 514, wherein the component includes an upper portion 538, and a lower portion 354, for example, the vial sleeve as opposed to the middle support, which rotate respective to one another and have corresponding slots within particular orientations, i.e. the open configuration, allow the boss to slide into an alignment ensuring feature, herein illustrated as the channel only when the valve is open, or closed, in a desired configuration and the alignment protrusion is properly placed into the ribs or channels 530. Otherwise, if not properly aligned the component will then not be allowed to slide completely into the receptacle 514 and protrude from a top surface of the secondary component nesting tray 510 indicating misalignment.

Additionally, as shown here, often components include portions which can be marred or otherwise damaged by a robotic grabbing component. In the present invention, the upper portion 538 includes a rubber plunger, which will later interact with an alternative component upper vial (not shown here), however it is readily understood that damaging of particular components can often be an issue, as such, proper alignment or provision of a particular grabbing area can often be desired.

In order to allow for proper grabbing on a more resistive or less fragile component, a de-nesting tool 550 can include a plurality of rods or pedestals which can engage or otherwise be pressed onto the secondary components 350 from a bottom portion when the secondary component nesting tray 510 is placed thereon thus partially ejecting the secondary components 350 partially from the nest and exposing a portion of the secondary component which is less fragile and can be better handled by the robot.

It will be appreciated that the degree of ejection can be varied in various implementations depending on the desired alignment or orientation. It will be appreciated that the various alignment or orientation features can be provided with a particular depth in an axial direction with respect to a given receptacle such that the orientation features are still engaged at the ejection height. In this manner, the risk of rotating the valve during the assembly or handling process out of a desired configuration is mitigated substantially. Further, as shown here, the orientation features can still be engaged at an ejection height, in this manner, even during removal of the part from the nest; there is no risk of rotating the valve during the removal process.

Figure 25:
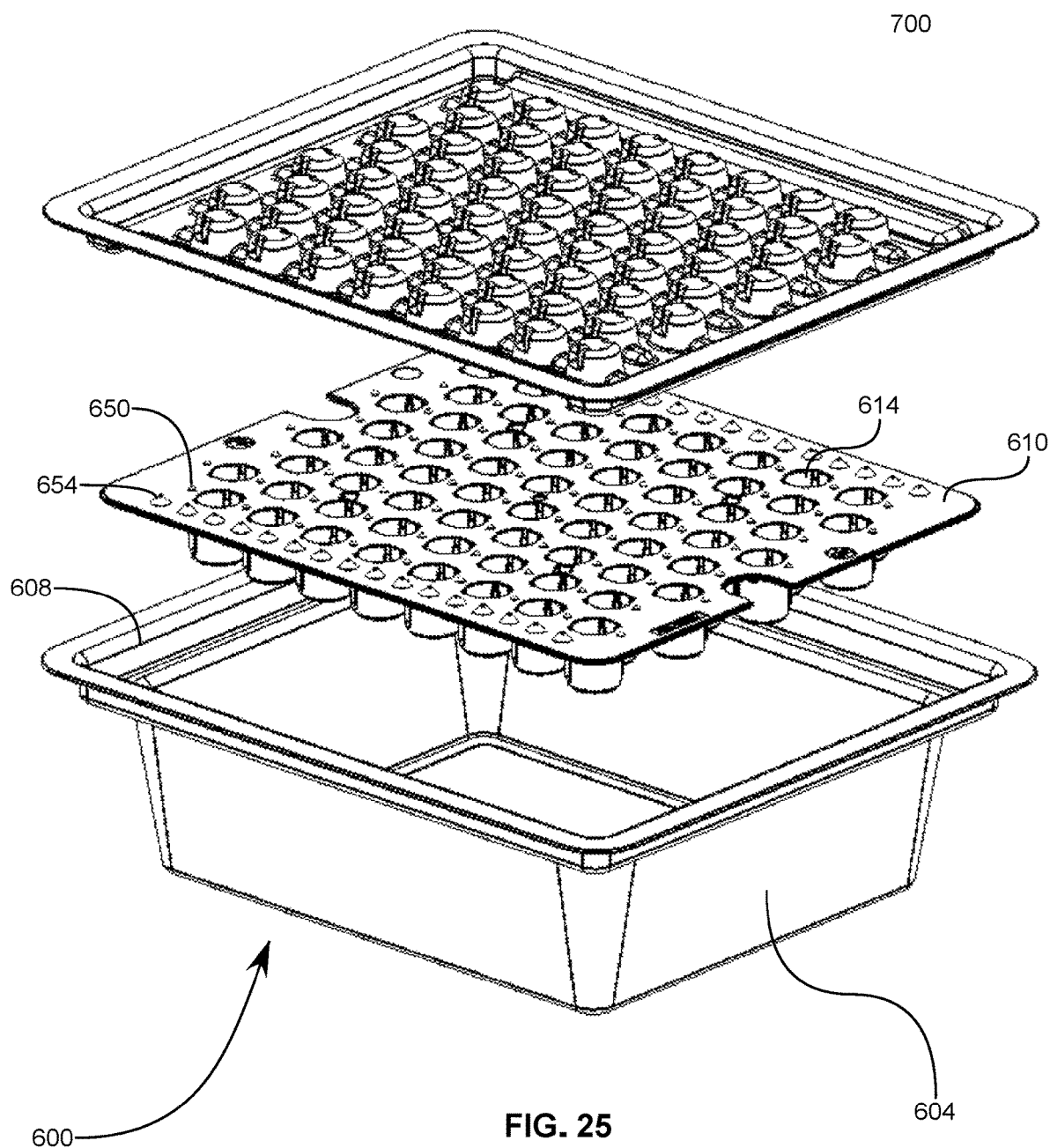
FIG. 25 illustrates an exploded side perspective view of yet another exemplary nest, tray, and lid assembly illustrative of various additional concepts of the present invention.
Figure 26A:
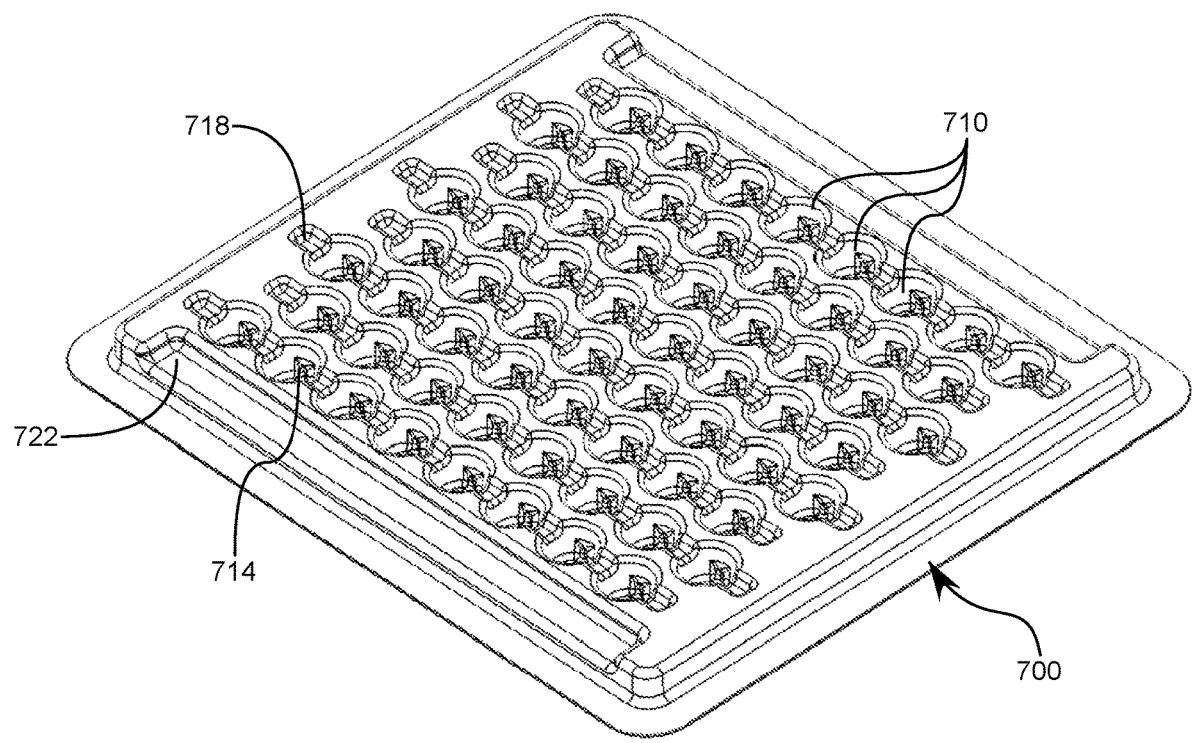
FIGS. 26A-B illustrated bottom perspective and bottom views of the exemplary lid of FIG. 25 illustrative of various additional concepts of the present invention.
Figure 26B:
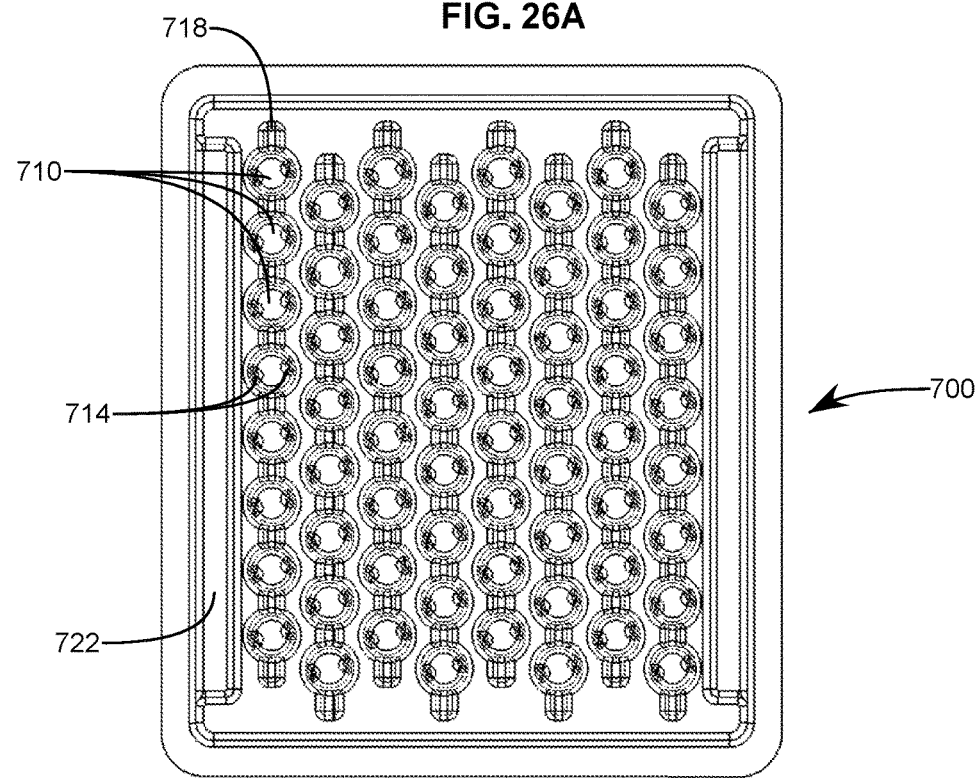
Figure 27:
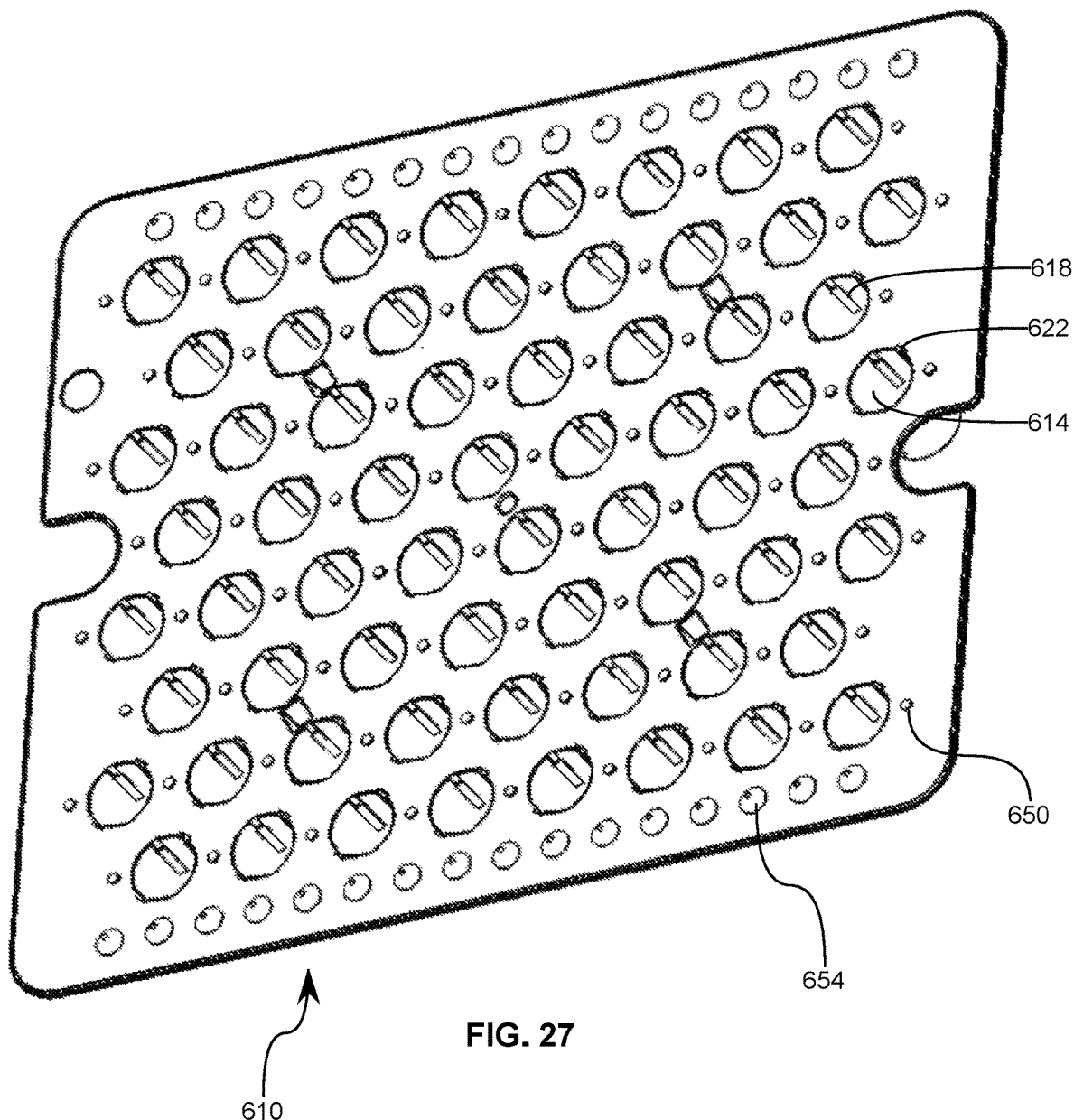
FIG. 27 illustrates an exploded side perspective view of yet another exemplary nest, tray, and lid assembly illustrative of various additional concepts of the present invention.

FIGS. 25-27 illustrate yet another embodiment of a nesting assembly 600 having another tub 604 having a recessed lip 608 for receiving an alternative primary nest 610 as shown. The primary nest 610 can also include various alignment features 618 and configuration ensuring features 622 on an internal surface of a plurality of receptacles 614. It will be appreciated that these alignment and configuration ensuring features, similar to above, can be provided about varying angular positions about the interior surfaces of the receptacles 614 so as to ensure the medical component is in a proper orientation or location with regard to the receptacle containing it, and that the medical component is in a proper configuration, i.e. valves in proper states, etc.

This embodiment also illustrates, as shown in FIGS. 25 and 27, that the nest 610 can be provided with a plurality of tool alignment features 650 and 654, wherein each receptacle can then have an associated tool alignment feature 650 provided at a specific radial distance from a central axis of each associated receptacle 614. This protrusion or feature can then be utilized by the tool itself in determining when properly aligned with a particular receptacle. The tool alignment features can also include edge or column alignment features 654 which can be configured to align with a particular column of receptacles 614 provided in the nest 610. As such, a particular machine can move the nest or the tool so as to provide proper alignment with an assembly arm or tool to remove components or place additional components onto medical components contained in the receptacles.

Also illustrated in this embodiment is an alternative lid or cover 700 which can be used in conjunction with any one of the bins and primary nests as discussed herein. The lid 700 can include a planar surface which fits within the recessed lip portion of the bin wherein the lid 700 can include a plurality of opposing receptacles 710. The opposing receptacles 710 can then fit over a medical component contained in the receptacles of the primary nest. The opposing receptacles 710 can also include a plurality of alignment or configuration ensuring features 714 which can maintain a particular alignment or configuration of any medical components contained within the primary nest by sandwiching the components therebetween. This lid and opposing receptacles can thus limit or reduce damage, shifting, or movement out of proper configuration of any medical components during transportation, etc.

In some embodiments, and as shown the bottom planar surface can extend downward into the bin from the upper recessed lip portion 608 so as to provide a compressive force on the primary nest. In some embodiments locking features, channels, ribs, etc., can be provided about opposing edge portions of the lid ant the bin so as to provide an interference or locking fit between the lid and the bin.

The lid 700 can also be provide with opposing recesses corresponding to the tool alignment features so as to allow for a flush fit between the primary nest and the lid without interference with the tool alignment features with a desired flush or compressive fit.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention. Additionally, any features, structures, components, method steps which are discussed in reference to any one of the aforementioned embodiments are readily adaptable for use into and with any features of the other alternative embodiments discussed herein, with the understanding that one of ordinary skill in the art will be capable of assessing the ability and be capable of making such adaptations.

What is claimed is:

1. A component storage and nest system, the system comprising:
   a tub having a lip portion provided on an interior surface of the tub;
      a primary nest having a plurality of receptacles extending from an upper surface thereof, the upper surface of the primary nest having a flange portion about a perimeter thereof being configured to engage the tub about the lip portion;
      a plurality of medical components, a medical component being provided in each of the plurality of receptacles of the primary nest; and
      a retainer nest having a plurality of pedestals extending from an upper surface thereof, the upper surface of the retainer nest having a flange portion about a perimeter thereof being configured to stack upon the flange portion of the nest retainer, each of the pedestals having an aperture formed in a base portion of the pedestals to allow a portion of each medical component to pass therethrough and where each pedestal is shaped to fit within the receptacles of the primary nest such that sidewalls of the pedestals abut sidewalls of the receptacles of the primary nest, and whereupon inserting the retainer nest into the primary nest causes the plurality of medical components to be held into place therebetween.

2. The component storage and nest system of claim 1, wherein the retainer nest includes one or more extensions protruding from the upper surface so as to align with the upper edge of the tub.

3. The component storage and nest system of claim 1, wherein the flange portion of the retainer nest and the flange portion of the primary nest stack upon one another within the tub on the lip portion so as to be flush with an upper edge of the tub.

4. The component storage and nest system of claim 1, wherein each receptacle of the primary nest has a base portion, and wherein a portion of the base portion of each receptacle is raised inward towards the upper surface of the primary nest.

5. The component storage and nest system of claim 1, wherein a portion of the sidewall of the pedestals of the retainer nest extend beyond the base portion thereof.

6. The component storage and nest system of claim 5, wherein the extended sidewall portion and perimeter about the aperture of the base portion of each pedestal of the retainer nest form a flared end, which is configured to seal with a complementary receiving end formed in a lower portion of each receptacle of the primary nest.

7. The component storage and nest system of claim 1, wherein a depth of the base portion of each pedestal of the retainer nest is greater than the portion of the medical component extending through the aperture towards the upper surface of the retainer nest.

8. The component storage and nest system of claim 1, wherein the primary nest and the retainer nest are configured to be inverted, such that the primary nest is resting on the retainer nest and can be removed to access each medical component that is now in an inverted state.

9. The component storage and nest system of claim 1, wherein the lip portion of the tub is provided at a predetermined distance from an upper edge of the tub.

10. The component storage and nest system of claim 9, further comprising a lid, the lid configured to seal the primary nest and the retainer nest within the tub.

11. The component storage and nest system of claim 1, further comprising a plurality of tool alignment features provided about the upper surface of the primary nest, at least one tool alignment feature being associated with each receptacle, each tool alignment feature being provided at a predetermined distance from a central axis of its associated receptacle.

12. The component storage and nest system of claim 1, further comprising:
 a lid, the lid having a plurality of opposing receptacles, the opposing receptacles having one or more alignment features provided on an interior surface thereof.

\* \* \* \* \*